United States Patent
Desu-Kalyanam

(10) Patent No.: US 10,123,679 B2
(45) Date of Patent: Nov. 13, 2018

(54) DEVICE FOR CLEANING AND DISINFECTING FOOTWEAR

(71) Applicant: Anu R. Desu-Kalyanam, Phoenix, AZ (US)

(72) Inventor: Anu R. Desu-Kalyanam, Phoenix, AZ (US)

( * ) Notice: Subject to any disclaimer, the term of this patent is extended or adjusted under 35 U.S.C. 154(b) by 403 days.

(21) Appl. No.: 14/752,952

(22) Filed: Jun. 28, 2015

(65) Prior Publication Data

US 2015/0297059 A1   Oct. 22, 2015

Related U.S. Application Data

(62) Division of application No. 14/218,827, filed on Mar. 18, 2014, now Pat. No. 9,101,260.

(51) Int. Cl.
*A47L 23/00* (2006.01)
*A47L 23/26* (2006.01)
(Continued)

(52) U.S. Cl.
CPC .......... *A47L 23/263* (2013.01); *A46B 13/023* (2013.01); *A46B 15/0034* (2013.01); *A47L 23/02* (2013.01); *A47L 23/20* (2013.01); *A61L 2/10* (2013.01); *B08B 1/002* (2013.01); *B08B 1/008* (2013.01); *B08B 7/0057* (2013.01); *A46B 2200/306* (2013.01); *A47L 23/00* (2013.01); *A47L 23/205* (2013.01); *A47L 2601/10* (2013.01); *A61L 2202/14* (2013.01); *B08B 1/00* (2013.01); *B08B 7/0035* (2013.01);
(Continued)

(58) Field of Classification Search
CPC .......... A46B 15/0034; A46B 2200/306; A47L 23/00; A47L 23/02; A47L 23/22; A47L 23/26; A47L 23/263; A47L 23/266; A61L 2/10; A61L 2202/14; A61L 2202/26
USPC .................. 15/36, 97.2, 161, 215, 216, 217; 250/455.11, 492.1; 422/24; 340/540
See application file for complete search history.

(56) References Cited

U.S. PATENT DOCUMENTS

| | | | | |
|---|---|---|---|---|
| 3,069,710 A | * | 12/1962 | Dremel | A47L 23/02 15/36 |
| 3,365,741 A | * | 1/1968 | Smagula | A47L 23/02 15/31 |
| 4,951,345 A | * | 8/1990 | Nappi, Sr. | A47L 23/263 15/302 |
| 5,466,248 A | * | 11/1995 | Whitson-Newman | A61N 5/0614 607/88 |

(Continued)

FOREIGN PATENT DOCUMENTS

| | | | | |
|---|---|---|---|---|
| EP | 0054523 A1 | * | 6/1982 | .......... A47L 23/263 |
| FR | 2233021 A1 | * | 1/1975 | .......... A47L 23/02 |
| FR | 2792208 A1 | * | 10/2000 | .......... A43D 3/1491 |

*Primary Examiner* — Michael Jennings

(57) ABSTRACT

Devices, systems and methods for cleaning and disinfecting footwear items are disclosed herein. In an aspect a cleaning belt element is configured to rotate a cleaning belt in a continuous loop around a first rotating cylinder and a second rotating cylinder wherein the first rotating cylinder and the second rotating cylinder are connected by the cleaning belt. In another aspect, a containment element is configured to receive the footwear item wherein the containment element comprises a shroud, one or more bristle protruding from at least one inside wall of the shroud, and a transparent floor layer wherein the received footwear item rests. In yet another aspect, an ultraviolet light element is configured to emit ultraviolet light from an ultraviolet light source wherein the ultraviolet light source is located below the transparent floor layer.

20 Claims, 17 Drawing Sheets

(51) Int. Cl.
*A46B 15/00* (2006.01)
*A61L 2/10* (2006.01)
*B08B 7/00* (2006.01)
*B08B 1/00* (2006.01)
*A47L 23/02* (2006.01)
*A46B 13/02* (2006.01)
*A47L 23/20* (2006.01)
*G01N 21/47* (2006.01)
*G01N 21/00* (2006.01)
*G01N 21/33* (2006.01)

(52) U.S. Cl.
CPC ............. *G01N 21/00* (2013.01); *G01N 21/33* (2013.01); *G01N 21/47* (2013.01)

(56) References Cited

U.S. PATENT DOCUMENTS

| | | | |
|---|---|---|---|
| 6,406,549 B1* | 6/2002 | Berg | A47L 23/263 134/1 |
| 8,617,479 B2* | 12/2013 | Gil | A61L 2/10 250/453.11 |
| 2002/0170132 A1* | 11/2002 | Brent | A47L 23/02 15/104.92 |
| 2003/0088297 A1* | 5/2003 | Stoppler | A61N 5/0614 607/94 |
| 2012/0045363 A1* | 2/2012 | Gil | A61L 2/10 422/24 |
| 2012/0324667 A1* | 12/2012 | Corlette | B60R 3/04 15/161 |

* cited by examiner

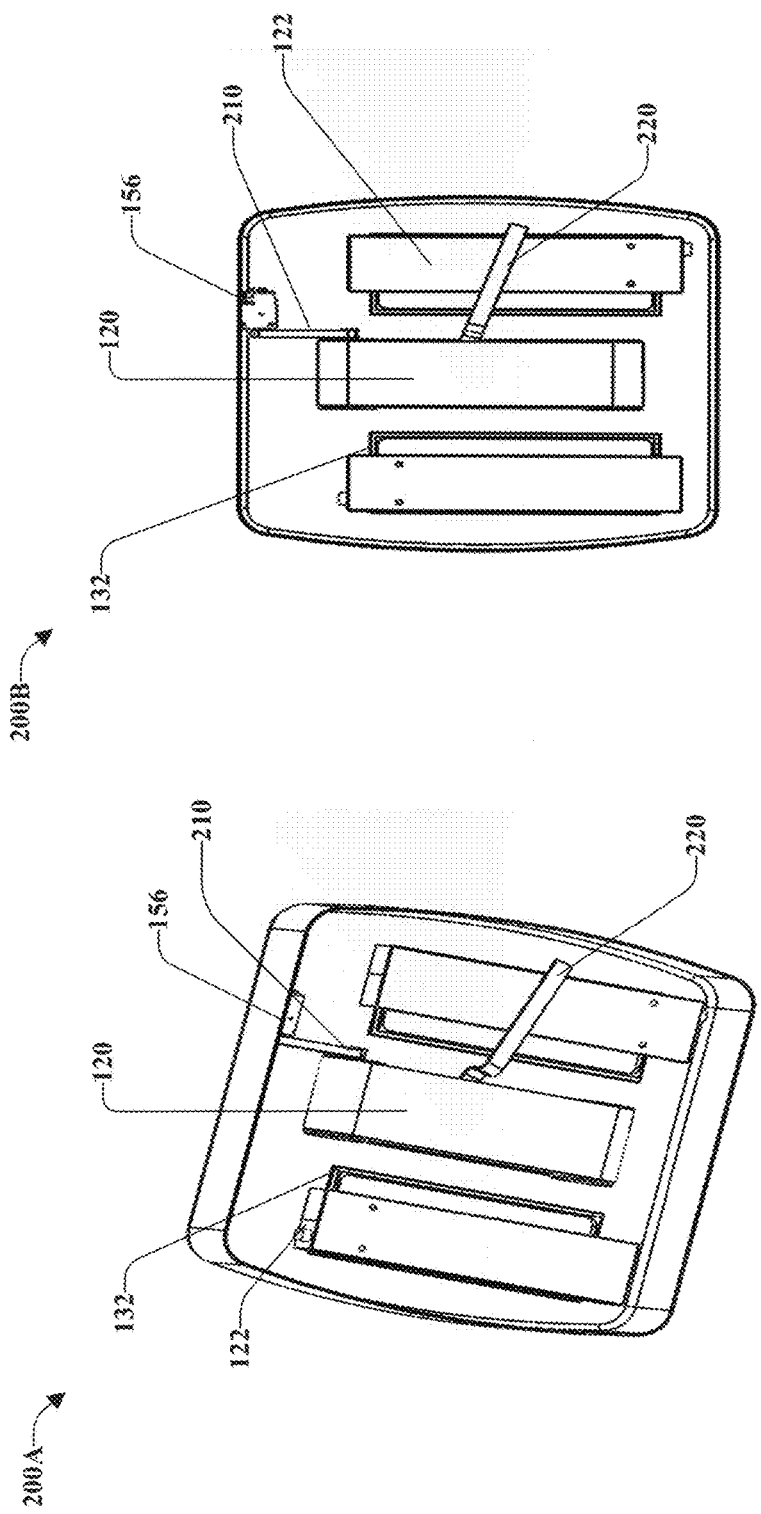

DEVICE FOR CLEANING AND DISINFECTING FOOTWEAR

CROSS REFERENCED TO RELATED APPLICATION

This divisional application claims the benefit of U.S. patent application Ser. No. 14/218,827, filed Mar. 18, 2014, and entitled "DEVICE FOR CLEANING AND DISINFECTING FOOTWEAR", the entirety of which application is hereby incorporated by reference herein.

TECHNICAL FIELD

This disclosure relates to a device and methods for cleaning and disinfecting footwear.

BACKGROUND

Traditionally, before entering an indoor establishment, such as a home, office or building, an entrant wipes his or her shoes (e.g. using a doormat, welcome mat, carpet, etc.). While the act of wiping shoes superficially removes some debris from the sole of the shoe, there still remain germs, debris, micro-organisms, bacteria, dirt, dust, and other such unsanitary matter. In an instance, a sample of shoes were found to have nine different species of bacteria including bacteria capable of causing stomach, eye, and lung infection. Often, coliform, a bacteria mostly derived from human and animal waste, can be found on footwear. Furthermore, in one research study, footwear was observed to transfer bacteria to tile floors in a house ninety percent of the time. Carpets are also known to harbor significant amounts of bacteria brought in from external sources. As compared to a toilet seat, which can be found to house thousands of bacteria, footwear can harbor millions of bacteria. The amount of unsanitary matter present on a person's shoes is generally understood.

Given the unsanitary nature of people's footwear, there exists a risk of transference of infection, bacteria, and viruses to indoor environments and the people who occupy such environments. For instance, children who often spend time on the floor playing are vulnerable to germs tracked into a home, especially provided some children are prone to placing hands in their mouth or using hands to rub their eyes. Generally, unsanitary material is easily tracked into homes, offices and other spaces as a result of insufficient cleaning and disinfecting of footwear prior to entering a space. Currently, the existing mechanisms for cleaning footwear are insufficient at disinfecting the footwear. There is a significant need for devices or tools to better disinfect, clean, and remove unsanitary matter from a person's footwear in an efficient and convenient manner.

SUMMARY

The following presents a simplified summary of the disclosure in order to provide a basic understanding of some aspects of the disclosure. This summary is not an extensive overview of the disclosure. It is intended to neither identify key or critical elements of the disclosure nor delineate any scope particular embodiments of the disclosure, or any scope of the claims. Its sole purpose is to present some concepts of the disclosure in a simplified form as a prelude to the more detailed description that is presented later.

In accordance with one or more embodiments and corresponding disclosure, various non-limiting aspects are described in connection with disinfecting and cleaning footwear. In accordance with a non-limiting embodiment, in an aspect, a device is provided comprising a cleaning belt element configured to rotate a cleaning belt in a continuous loop around a first rotating cylinder and a second rotating cylinder wherein the first rotating cylinder and second rotating cylinder are connected by the cleaning belt; a containment element configured to receive the footwear item wherein the containment element comprises a shroud, one or more bristle protruding from at least one inside wall of the shroud, and a transparent floor layer wherein the received footwear item rests; an ultraviolet light element configured to emit ultraviolet light from an ultraviolet light source wherein the ultraviolet light source is located below the transparent floor layer and the emitted ultraviolet light passes through the transparent floor layer wherein the emitted ultraviolet light is absorbed by the footwear item and material located at the footwear item; and a display element configured to present information or data in connection with cleaning or disinfecting the footwear item.

The disclosure further discloses a method, comprising rotating a cleaning belt around at least two rotating cylinder connected by the cleaning belt wherein the cleaning belt rotate in a continuous loop around the at least two rotating cylinder; contacting the cleaning belt with a footwear item surface during the cleaning belt rotation; inserting the footwear item into a receptacle bound by four walls, a four walled shroud covering comprising one or more bristle protruding from at least one inside wall of the shroud covering, and a transparent floor layer that supports a base of the footwear item; emitting ultraviolet light from an ultraviolet light source wherein the emitted ultraviolet light passes through the transparent floor layer and the emitted ultraviolet light is absorbed by the footwear item and unsanitary matter located at the footwear item; and displaying information or data related to cleaning or disinfecting the footwear item. In an aspect the ultraviolet light source can move along at least one surface of the footwear item while the ultraviolet light source emits ultraviolet light.

The following description and the annexed drawings set forth certain illustrative aspects of the disclosure. These aspects are indicative, however, of but a few of the various ways in which the principles of the disclosure may be employed. Other advantages and novel features of the disclosure will become apparent from the following detailed description of the disclosure when considered in conjunction with the drawings.

BRIEF DESCRIPTION OF THE DRAWINGS

FIG. 2A illustrates an example non-limiting device for cleaning and disinfecting footwear from an angled bottom view.

FIG. 2B illustrates an example non-limiting device for cleaning and disinfecting footwear from a bottom view.

DETAILED DESCRIPTION

Overview

Figure 1A:
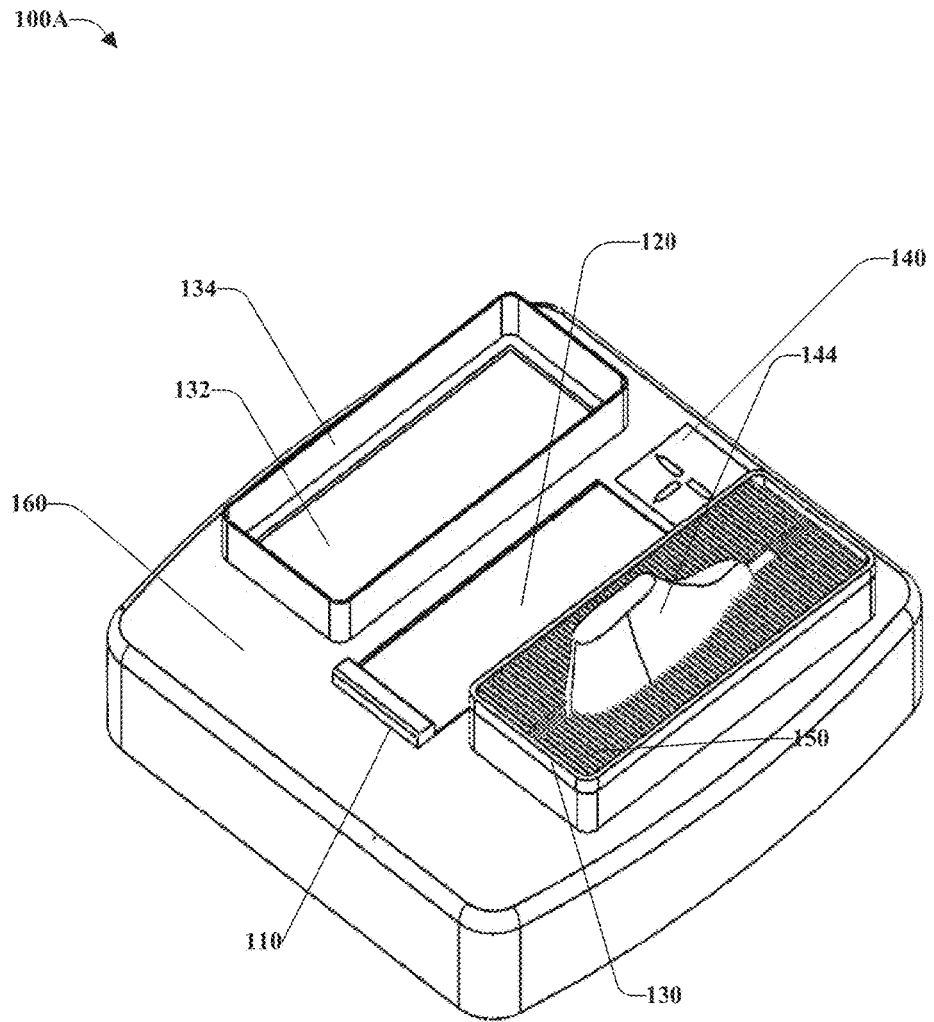
FIG. 1A illustrates an example non-limiting device for cleaning and disinfecting footwear.

The innovation is now described with reference to the drawings, wherein like reference numerals are used to refer to like elements throughout. In the following description, for purposes of explanation, numerous specific details are set forth in order to provide a thorough understanding of this innovation. It may be evident, however, that the innovation can be practiced without these specific details. In other instances, well-known structures and components are shown in block diagram form in order to facilitate describing the innovation.

By way of introduction, the subject matter disclosed in this disclosure relates to an automated device for cleaning footwear. In some embodiments, the device is designed to facilitate disinfection, removal of debris, and general cleaning of a user's footwear in an easy to use, automated, quick manner. In some embodiments, the device can include an automated cleaning belt functionalized with material layers (e.g. Velcro, bristles, etc.) to remove debris and unsanitary material from the footwear. In other embodiments, the device can include one or more ultraviolet light sources that emit ultraviolet light toward various surfaces of the footwear thereby disinfecting the footwear by killing bacteria and other organisms present on the footwear. Furthermore, the device can include a display console to present information to a user regarding the cleaning and disinfecting of the footwear.

The device, in some embodiments, can be portable (e.g. possess a handle for carrying) and has automated characteristics whereby the user may control the device (e.g. via remote, phone, switch console, etc.), however the cleaning and disinfecting operations of the device are automated. An automated cleaning belt performs cleaning functions to remove debris, objects, and unwanted matter from the footwear. Also, the ultraviolet light will disinfect the footwear. In an aspect, a device embodiment can also incorporate spraying a disinfectant solution onto the footwear to kill particular organisms or bacteria. Furthermore, in an aspect, larger debris can be vacuumed or suctioned into a device compartment for later disposal. It should be appreciated that various embodiments herein may utilize a variety of mechanical technologies (e.g. motors, pulleys, power source, sensors, etc.) having different properties. Accordingly, an automated device for cleaning and disinfecting footwear as well as the elements that comprise such device are described herein.

Example Device for Cleaning and Disinfecting Footwear

Figure 1B:
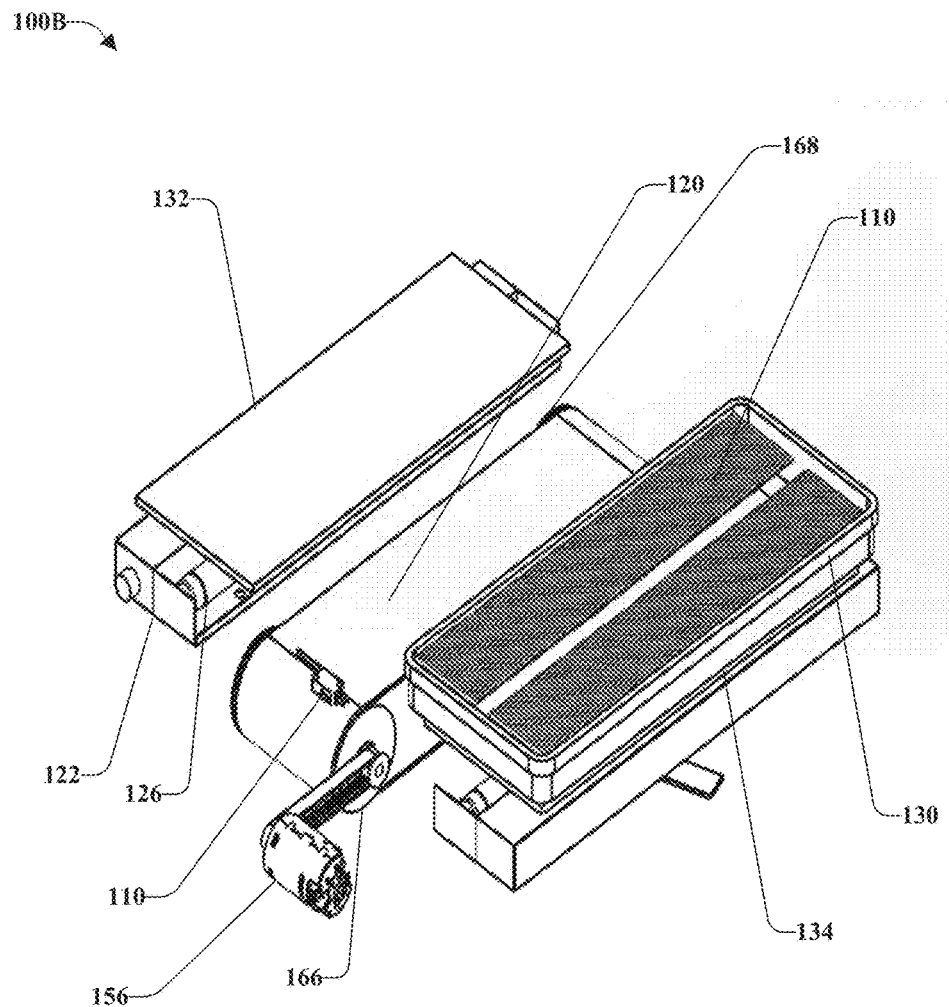
FIG. 1B illustrates an example non-limiting device for cleaning and disinfecting footwear including an ultraviolet light element, a transparent floor layer, a motor element, a cleaning belt element, a shroud element, a containment element, and a one or more bristle element.

Referring now to the drawings, with reference initially to FIGS. 1A and 1B, illustrated are example devices 100A, 100B, and 100C according to various embodiments of the subject disclosure. Turning now to FIG. 1A, device 100A is depicted wherein device 100A comprises several elements capable of cleaning and disinfecting footwear. In an aspect, device 100A-C can comprise a cleaning belt element 120 configured to rotate a cleaning belt in a continuous loop around a first rotating cylinder 166 and a second rotating cylinder 168 wherein the first rotating cylinder 166 and second rotating cylinder 168 are connected by a cleaning belt 120; a containment element 134 configured to receive the footwear item wherein the containment element 134 comprises a shroud 130, one or more bristle 150 protruding from the inside wall of the shroud, and a transparent floor layer 132 (e.g., illustrated at FIG. 1B) wherein the received footwear item rests; an ultraviolet light element 122 (e.g., illustrated at FIG. 1B) configured to emit ultraviolet light wherein the ultraviolet light element is located below the transparent floor layer and the emitted ultraviolet light passes through the transparent floor layer wherein the emitted ultraviolet light is absorbed by the footwear item and unsanitary matter located at the footwear item; and a display element 140 configured to present information or data in connection with cleaning the footwear item 144.

In an aspect, device 100A-C can employ a variety of mechanisms to clean footwear item 144. For instance, cleaning belt element 120 employs a cleaning belt capable of rotating and removing matter from footwear item 144. In an aspect, the cleaning belt element 120 can employ a material layer attached to the surface of the cleaning belt. The material layer can comprise a material of suitable composition for removal of debris, dust, pebbles, unsanitary matter and other items present on footwear item 144. In an instance, the material layer can comprise fabric arranged in a hook and/or loop array such as Velcro (e.g., comprising a material such as cotton, nylon, Teflon, or polyester). In another instance the material layer can comprise bristles such as wire bristles for brushing off debris from the footwear item 144. The material layer can comprise of any such material that can remove matter from the footwear item 144 in connection with the movement of the cleaning belt.

In an aspect, cleaning belt element 120 is configured to rotate the cleaning belt in a continuous loop around one or more pulley 146 (e.g., illustrated at FIG. 1B). The mechanism can comprise of a first rotating cylinder 166 and a second rotating cylinder 168 connected by the cleaning belt 120 wherein the first rotating cylinder 166, second rotating cylinder 168 and the cleaning belt 120 can support the footwear item 144. Illustrated at device 100A-C are two rotating cylinders and cleaning belt element 120 absent a pulley mechanism. However, in an embodiment, the device can implement a one or more pulley comprised of cables, rope or string-like material to connect the first rotating cylinder 166 and the second rotating cylinder 168. In an aspect, a one or more pulley (not illustrated in any figure) can facilitate the rotation of the first rotating cylinder 166 and the second rotating cylinder 168 and thereby the rotation of the cleaning belt 120 encircling the first rotating cylinder 166, second rotating cylinder 168 and one or more pulley. Furthermore, in an embodiment, the first rotating cylinder 166 and/or second rotating cylinder 168 can comprise a cylinder or in some embodiments two wheels connected by an axle respectively. The rotating cylinder mechanism can be any variety of cylinders (e.g. smooth, textured, etc.) comprising various materials (e.g., metal, plastic, etc.). In another embodiment, a wheel structure (not illustrated) capable of rotating and interconnecting with a pulley system can be implemented. In other embodiments, the cleaning belt and one or more pulley can connect two or more wheel and axle elements to form an integrated pulley system for rotating cleaning belt element 120. In an aspect, device 100A-C can comprise a motor element 156 (e.g., illustrated at FIG. 1B) configured to convert (e.g., provided by a power source connected to device A-C) electricity into mechanical motion including, but not limited to, rotation of the first rotation cylinder 166, a one or more pulley, or luminescence of the one or more ultraviolet light element 122 (e.g., illustrated at FIG. 1B).

Further, the motor element 156 can provide mechanical motion to the first rotating cylinder 166 thereby rotating the cleaning belt 120 of cleaning belt element 120 (which rests around the first rotating cylinder 166 and second rotating cylinder 168) in a continuous loop. In an aspect, the motor element 156 can generate a rotational movement and transfer the rotational movement to the first rotating cylinder 166 via a connector belt that connects the motor element 156 to the first rotating cylinder 166 to be further discussed herein. The movement of cleaning belt element 120 thereby facilitates the material layer of the cleaning belt to contact one or more surface of footwear item 144 during the cleaning belt rotation thereby removing debris and matter from the footwear item 144. For instance, the cleaning belt element 122 can comprise a material layer at its surface wherein the material layer comprises hooks and loops. Upon rotation of the cleaning belt element 120, the friction and contact between a surface of the footwear item 144 (e.g. bottom of a shoe), and the rotating hook and loop of the material layer can dislodge, bind (to the hook or loop), and remove debris as well as unsanitary matter from the footwear item 144 surface.

In another aspect, device 100A-C can further comprise heel stop element 110, which, in connection with the cleaning belt element 120, is configured to start the cleaning belt rotation or stop the cleaning belt rotation (e.g. in connection with one or more pulley 146 and motor element 156). The heel stop element 110 can provide support for footwear item 144. For instance, wherein footwear item 144 is a shoe (e.g., sneaker, dress shoe, sandal, boat shoe, etc.), the heel of the shoe can be rested against the heel stop element 110, which is an elevated portion of device 100A-C at the base of the cleaning belt element 120. The heel stop element 110 can hold a footwear element 144 stationary (e.g. propping a shoe heel against the heel stop element 110) by serving as a support wall.

Also, in an aspect, heel stop element 110 can employ a switch mechanism to commence and terminate the continuous rotation of cleaning belt element 120. The switch can implement a click mechanism wherein by pressing or releasing the clickable switch with the footwear item 144 (e.g. heel of a shoe) the rotation of cleaning belt element 120 can turn on or off respectively. For instance, a user can support a shoe heel on the heel stop element 110 and the pressure applied by the shoe heel to the heel stop element 110 can click the associated switch "on" thereby commencing the rotation of cleaning belt element 120. Accordingly, removal of the shoe heel from heel stop element 110 can release the clicking mechanism thereby turning the switch "off", wherein the rotation of cleaning belt element 120 is arrested. In another aspect, the heel stop element 120 can employ a sensor system wherein one or more sensor associated with the heel stop element 110 can detect the presence of a footwear item 144. The sensor can send a signal to the motor to commence rotation of the cleaning belt element 120 in accordance with detecting the presence of a footwear item 144. Similarly the sensor can send a signal detecting the absence of a footwear item 144 thereby arresting rotation of the cleaning belt element 120.

In another embodiment, device 100A-C can comprise a containment element 134 configured to receive the footwear item 144 wherein the containment element 134 comprises a shroud 130, one or more bristle 150 protruding from the inside wall of the shroud 130, and a transparent floor layer 132 wherein the received footwear item 144 rests. In an aspect, containment element 134 is a cavity for receiving footwear item 144. Furthermore, shroud 130 can be inserted or snapped into the cavity of containment element 134. In an aspect, shroud 130 can be interchangeable (e.g. inserting the shroud 130 component into the containment element 134), thus the entire unit can be removed for cleaning or disposal and a clean or new shroud 130 can be inserted into containment element 134. In an aspect, shroud 130 can be lined with bristles that extend from the inner wall of shroud 130. In an embodiment, the bristles can extend from the front wall. In another embodiment, the bristles can extend from more than one wall. In yet another embodiment, one or more bristle can extend from the walls of the containment element 134, shroud 130, or the containment element 134 inside wall. For example, in an embodiment, the one or more bristle can extend from the top wall of the containment element 134 wherein the one or more bristle can seal around footwear item 144. Thus a user can push the toe area of a shoe into the front wall of one or more bristles thereby closing in around the shoe and holding it stationary.

Furthermore, in an aspect, the floor of containment element 134 is comprised of a transparent floor layer 132. Additionally, located below the transparent floor layer 132 is ultraviolet light element 122 (e.g., illustrated in FIG. 1B). Furthermore, the containment element 134 comprises a transparent floor layer 132 to allow the emitted UV light (e.g. using ultraviolet light element 122) to pass over and illuminate one or more surface of footwear item 144.

Device 100A-C can employ more than one containment element 134, wherein the position of each containment element 134 can be arranged in various non-limiting positions according to multiple embodiments. In an instance, device 100A-C can employ a left containment element 134 and a right containment element 134 wherein each containment element 134 can receive a left footwear item 144 and a right footwear item 144 respectively. By employing more than one containment element 134, device 100A-C can allow a user to facilitate cleaning of two footwear items 144 (e.g., pair of shoes) simultaneously.

Turning now to FIG. 1B, illustrated are additional elements of device 100A. In an embodiment, device 100A-C employs an ultraviolet light element 122 configured to emit ultraviolet light from an ultraviolet light source 126 wherein the ultraviolet light source 126 is located below the transparent floor layer 132 and the emitted ultraviolet light passes through the transparent floor layer 132 wherein the emitted ultraviolet light is absorbed by the footwear item 144 and unsanitary matter located at the footwear item 144. In an aspect, the ultraviolet light element 122 employs one or more ultraviolet light sources 126 capable of disinfecting a footwear item 144. By emitting ultraviolet (UV) light, at various wavelengths (e.g. short wavelengths, UV-C spectrum, etc.) toward footwear item 144, the UV light kills microorganisms, fungi, yeasts, harmful pathogens, microbial organism, viruses, bacteria and bacterial spores present on the exposed surfaces and within crevices of footwear item 144.

In an aspect, the UV light can destroy the nucleic acid of the microorganism and unsanitary bacteria by UV radiation, thereby rendering the microorganism unable to perform functions essential for living. Furthermore, the ultraviolet light element 122 can employ settings to adjust variable characteristics related to the emission of UV light such as the wavelength, duration of footwear item 144 exposure to UV light, intensity of light exposure, power fluctuations of the UV light, pulsing the UV light at various rates, and other such variables capable of adjustment for specific disinfecting purposes.

In an aspect, the UV light element 122 can employ one or more various types of UV light sources 126 (e.g. UV lamps, UV light-emitting diodes, UV lasers, mercury vapor lamps, xenon lamps, fluorescent lamps, excimer lamp, argon lamps, deuterium lamps, magnesium fluoride lamps, gas-discharge lamps, UV light source capable of emitting UV-C wavelength, etc.). Furthermore, in an aspect, ultraviolet light element 122 can employ one or more UV light source 126 of various size or shape. In an embodiment, the ultraviolet lamp can emit Ultraviolet C light (e.g., in the wavelength range of 280-100 nm). In other embodiments, the ultraviolet lamp can emit ultraviolet A, ultraviolet B, near ultraviolet, middle ultraviolet, or far ultraviolet wavelengths. Furthermore, in an embodiment, the UV light element 122 can employ a sliding mechanism in coordination with the UV light source 126 in order to emit UV light along various areas and surfaces of footwear item 144. Upon illumination of the UV light source, the emitted light rays pass through transparent floor layer 132. In an aspect, transparent floor layer 132 can take the form of any material allowing light to pass through including, but not limited to, glass (e.g. light absorbing glass, light scattering glass, etc.).

Most of the emitted UV light targets one or more surface of footwear item 144 thereby killing the microorganisms present on such footwear item 144. The one or more bristle 150 can absorb the UV light not absorbed by footwear item 144. As a footwear item 144 passes through shroud 130 and into containment element 134, the one or more bristle 150 deflect downward and then upward to completely nestle around footwear item 144. In an aspect, by completely circumscribing footwear item 144, the one or more brush 150, absorbing any UV light not absorbed by footwear item 144 or deflected off a surface of footwear item 133. Thus, the one or more bristle 150 effectively blocks the UV light from making contact with any object (e.g. a person, skin, etc.) outside of containment element 134. Furthermore, in an aspect, shroud 130 contains the emitted UV light within the shroud 130 interior walls thereby also preventing any UV light exposure beyond containment element 134.

In an aspect, another function of one or more bristle 150 is the ability to remove matter; debris and unsanitary items from footwear item 144 by effectively brushing items clear of footwear item 144. In an instance, device 100A-C can employ a vacuum element configured to suction matter removed from footwear item 144 into a designated area. Furthermore, in an embodiment, device 100A-C can employ a collection tray element that stores collected material removed from the footwear item 144. In an aspect, the vacuum can create airflow to force the matter, debris, and unsanitary items from the containment element 134 to the collection tray element. The collection tray element can be removed and reinstalled for easy disposal of the collected material, unsanitary material, and debris.

Often a user of device 100A-C can appreciate the convenience of using the device for cleaning footwear. For instance, the user may not wish to remove a pair of shoes before entering a home or office. The user may take satisfaction in removing debris and unsanitary matter as well as scanning the shoes with a UV light to remove bacteria, microorganisms and viruses from the shoes, such that the user after performing cleaning by device 100A-C will enter an establishment without removing the shoes. Furthermore, the device 100A-C offers convenience in its ability to automate the task of cleaning footwear. For instance, cleaning belt element 120 can be automatically rotated through employment of a motor, power source, pulleys, and sensor system. The device 100A-C lessens the burden to a user associated with manually wiping footwear against a cleaning surface such as a doormat.

Similarly, the disinfection feature of device 100A-C provided by UV light element 122 can be automated. In an aspect, device 100A-C can employ a sensor element configured to send a signal upon detecting the presence of the footwear item 144 within containment element 134. In an aspect, the sensor can detect the presence of footwear item 144 (e.g., upon receipt of the shoes into the containment element 134). A sensor located within or near containment element 134, ultraviolet light element 122, or at another such location can perform detection tasks through any of a variety of mechanisms including, but not limited to, motion detection, temperature detection, light detection, magnetic field detection, vibration detection, pressure detection, sound detection, humidity detection, moisture detection, laser detection and other such mechanisms. The sensor (referred to as first sensor) is capable of sending a signal to another sensor (referred to as second sensor) upon detection of the presence of footwear item 144.

Furthermore, in an aspect, a second sensor element receives the signal sent by the first sensor element. Upon receipt of the signal, the second sensor element can send a signal to the ultraviolet light element 122 to commence illumination of the UV light for purposes of disinfecting the footwear item 144. In another embodiment, the first sensor element, second sensor element, or other such sensor element can send a signal to any number of additional sensors (e.g., a third sensor element, a fourth sensor element, etc.) wherein the additional sensors can trigger the activity of other elements of device 100A-C. For instance, a sensor can detect the presence of a footwear item 144 at heel stop element 110 and send a signal to a sensor associated with cleaning belt element 120 thereby commencing rotation of cleaning belt 120. In an aspect, the sending and receipt of signals in connection with one or more sensor can activate the operation of any one or more elements of device 100A-C individually or simultaneously. For example, a user can place a left shoe on the cleaning belt 120 and the right foot within a right containment element 134 wherein both sensors associated with the respective elements can activate the operation of each element upon detection of a footwear item 144. An activation of a left containment element 134 and a right containment element 134 can also occur simultaneously. In some embodiments, the incorporation of sensors within devices 100A-C and can enable significant automated benefits to the user.

In another embodiment, device 100A-C can employ a remote control element capable of controlling one or more function related to the device via a wireless remote control mechanism or one or more device switch. The remote control element can interact with the sensors by sending signals to such sensors thereby activating the operation of various elements. In an aspect, a remote control can be designed specifically to function with devices 100A-C. In another aspect, a mobile device can act as a remote control, wherein a user can download an application to enable such mobile device (e.g., tablet computers, mobile phones, smart phones, mobile computers, laptops, etc.) to control various device 100A-C functions. For instance, a mobile device can function as a remote control to power on and off the device, change the device settings (e.g. ultraviolet light element 122 characteristics, rotational speed of cleaning belt element 120, information displayed at display element 140, etc.). In an embodiment, a mobile device can be implemented as a device controller by use of infrared signal transmission, wherein the commands given from the mobile device are converted into infrared signals. Furthermore, applications can be developed or implemented to utilize the mobile device as a controller for devices 100A-C. In another embodiment, device 100A-C can incorporate a set of switches to control the device located on the device itself. The switches can comprise buttons, touch mechanisms, or other such controls to adjust or control device operation.

In another aspect, device 100A-C can employ a display element 140 configured to present information or data in connection with cleaning the footwear item. In an aspect, the display element can present information such as the level of completion of the cleaning cycle. For example, the display element 140 can inform a user that the cleaning cycle is 40% complete, requires three minutes until a cleaning cycle is complete, has disinfected the shoe to a particular confidence level, or present other such information. In an aspect, display element 140 can present digital alphanumeric information or display graphics to convey information related to device operation to the user. In an example, display element 140 can present a graphic display of an object along the left side of the display, the right side of the display, and the center of the display. The graphic can illuminate, blink, flash, or convey a distinguishing characteristic to coincide with the element or elements of devices 100A-C in active operation at a particular time. For instance, if a user places a right shoe in the right containment element 134 and a left shoe against heel stop element 110, the right indicator graphic (e.g. a graphic of a shoe) and the central indicator graphic can illuminate at display element 140. In an aspect, display element 140 can comprise a variety of display technologies such as an LED screen, LCD screen, touch screen, hi definition screen, VGA screen, and other such display screen technologies.

Figure 1C:
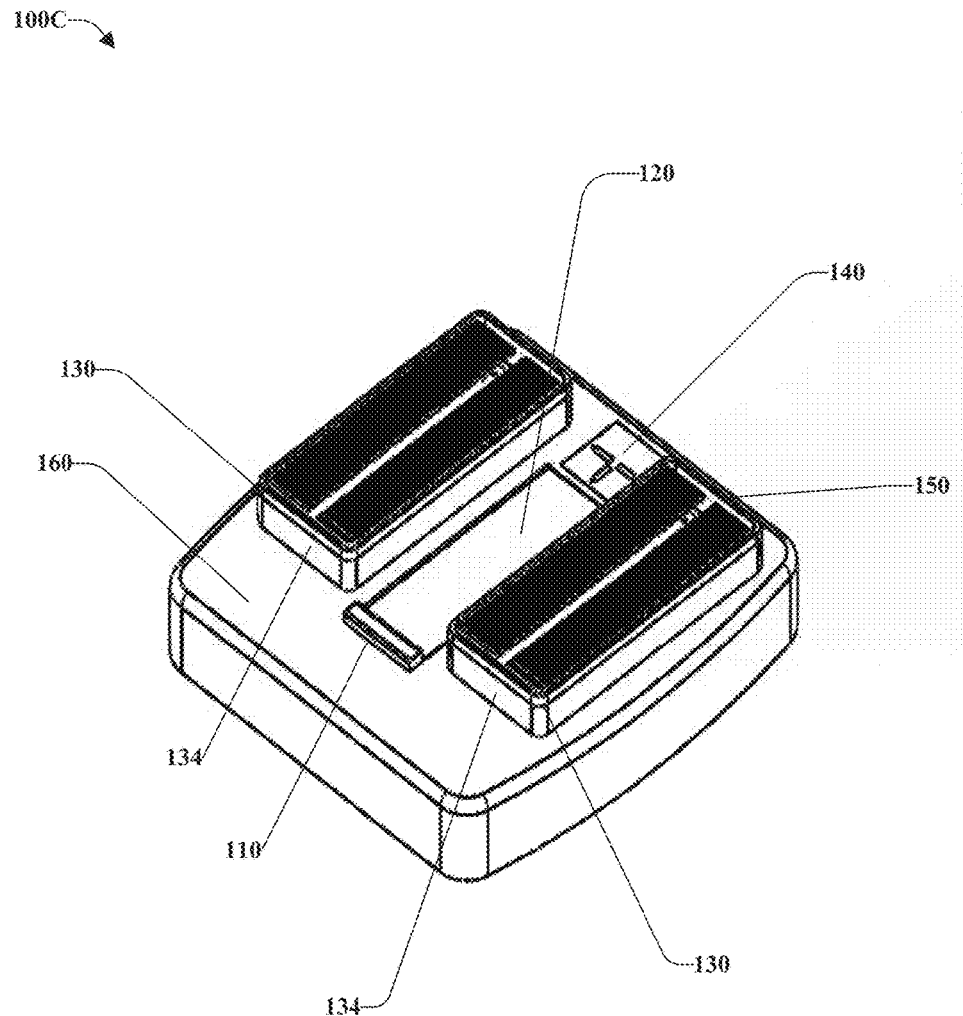
FIG. 1C illustrates an example non-limiting device for cleaning and disinfecting footwear from a topside view.

In an embodiment, device 100A-C can employ a device casing 160 to protect internal elements, provide aesthetic beauty, and house the integrated device elements within a monolithic structure. In an aspect, device casing 160 can take the form of any of a variety of materials such as plastic, metal, glass, wood, and so on. Various elements can reside within the device casing 160 such as motor element 156, UV light element 122, a power element, and other such elements (such as those illustrated at FIG. 1A, FIG. 1B, and FIG. 1C). The surface of device casing 160 can also circumscribe various elements such as display element 140, containment element 134, cleaning belt element 120 and other such elements (such as those illustrated at FIG. 1A-C). In an embodiment, FIG. 1C illustrates a non-limiting embodiment of a cleaning device 100C in the absence of footwear item 144 within containment element 134. The cleaning device 100C illustrates a left containment element 134 (e.g., to house a left shoe), a right containment element 134 (e.g., to house a right shoe), a left shroud 130 (e.g., to cover a left shoe), a right shroud (e.g., to cover a right shoe), a cleaning belt element 120, a display element 140, a heel stop element 110, a device casing 160, and one or more bristle 150.

Turning now to FIGS. 2A and 2B are bottom views of devices 200A and 200B. In an aspect, device 200A illustrates depicts the underside of a cleaning and disinfecting device depicted at an angle. Furthermore, device 200B illustrates a straight on view of the underside of a cleaning and disinfecting device. In an aspect, devices 200A-B illustrate ultraviolet light element 122, transparent floor layer 132, cleaning belt element 120, motor element 156, tension arm element 220, and connector belt element 210. In an aspect, connector belt element 210 is configured to connect motor element 156 to a first rotating cylinder 166 of cleaning belt element 120. The connector belt element 210 can transfer rotational motion sourced at motor element 156 to the first rotating cylinder 166, and the second rotating cylinder 168. The connector belt element 210 can be circumscribed around a rotational element affixed to motor element 156 and also circumscribed around a fixed protrusion extending from the first rotating cylinder 166. As the motor element 156 converts electricity into rotational movement, the rotational element begins to rotate, thereby rotating connector belt element 210, which rotates the first rotating cylinder 166 (e.g., via the fixed protrusion extending from the first rotating cylinder 166). Furthermore, the first rotating cylinder 166 upon rotation, activates the rotation of the second rotating cylinder 168 thereby rotating cleaning belt element 120. Thus connector belt element 210 can serve as a conduit to facilitate translation of the rotational motion sourced from motor element 156 as transferred to the cleaning belt element 210 (e.g. via the first rotating cylinder 168).

In another aspect, devices 200A-B illustrates tension arm element 220 configured to maintain the cleaning belt tautness. In an aspect, cleaning belt 120 is susceptible to forming belt slack during rotation wherein such slack could diminish the level of contact between the cleaning belt 120 and the footwear item 144 surfaces. To eliminate such susceptibility, tension arm element 220 maintains the tautness of cleaning belt element 220 by applying additional force to the belt during rotation. In an aspect, tension arm element 220 can form a support arm to prevent drooping or slack from accumulating at the cleaning belt element 120. The tension arm element 220 can create tension within the belt by applying forces along a surface of cleaning belt element 120. In an embodiment, more than one tension arm element 220 can be applied to cleaning belt element 120 to maintain an efficacious level of tautness as to allow cleaning belt 120 to remove debris and material from footwear item 144. Furthermore, the level of tautness can be adjusted to increase, decrease, or maintain tautness.

Figure 3:
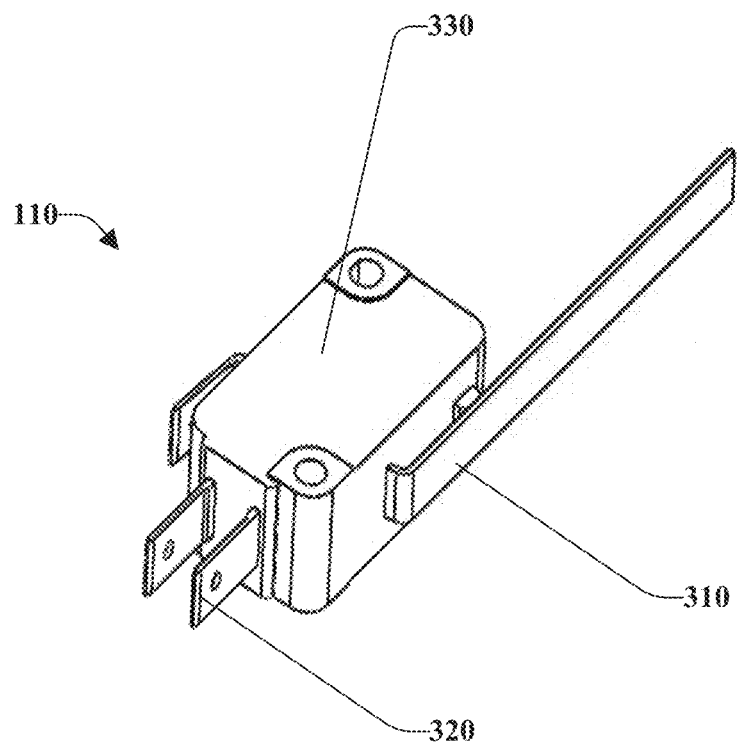
FIG. 3 illustrates an example non-limiting heel stop element of a cleaning and disinfecting device.

Turning now to FIG. 3, illustrated is an isolated depiction of heel stop element 110. In an aspect, heel stop element 110 can comprise a variety of elements. In an aspect, heel stop element 110 can incorporate a switch (e.g., micro switch) mechanism described above in order to automatically start and stop the rotation of cleaning belt element 120. In a non-limiting embodiment, the switch is depicted by clickable arm 310 wherein a heel of footwear item 144 can rest against such arm or depress the arm to begin rotation of cleaning belt element 120. Upon pressure release of clickable arm 310, the rotation of cleaning belt element 120 will arrest. In another aspect, electrical prong 320 facilitates the uptake of electricity to heel stop element 110 by tapping into an electrical power source. Furthermore, in an aspect, encasement 330 can implement sensors for detection of a footwear item 144 or any circuitry, mechanics, or equipment required to facilitate the automated feature of heel stop element 110.

Figure 4:
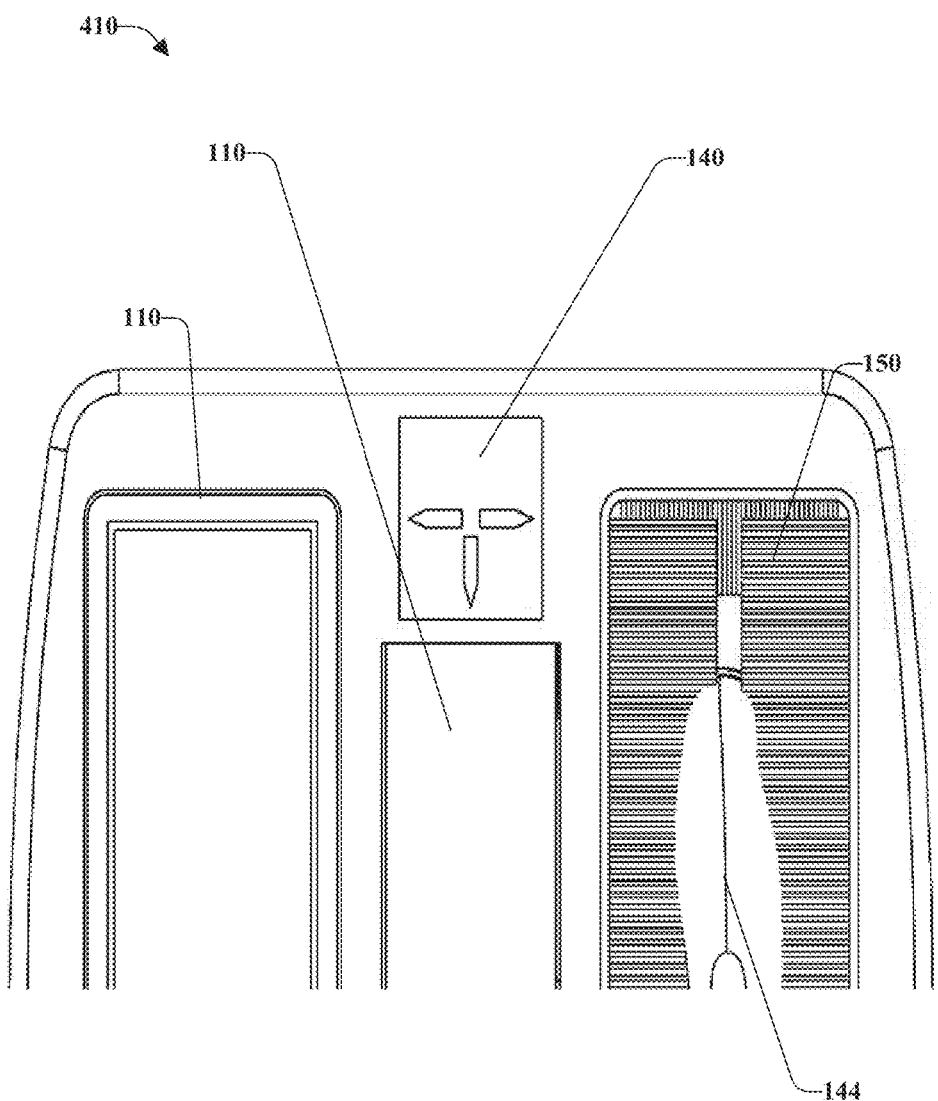
FIG. 4 illustrates an example non-limiting device for cleaning and disinfecting footwear magnifying the top front portion of the device.

Turning now to FIG. 4, illustrated is a magnified view of the top surface of the upper half of device 400. In an aspect, the illustration depicts cleaning belt element 120, display element 140, containment element 134, footwear item 144, one or more bristle 150, and shroud 130. The elements are illustrated at a magnified view.

Figure 5A:
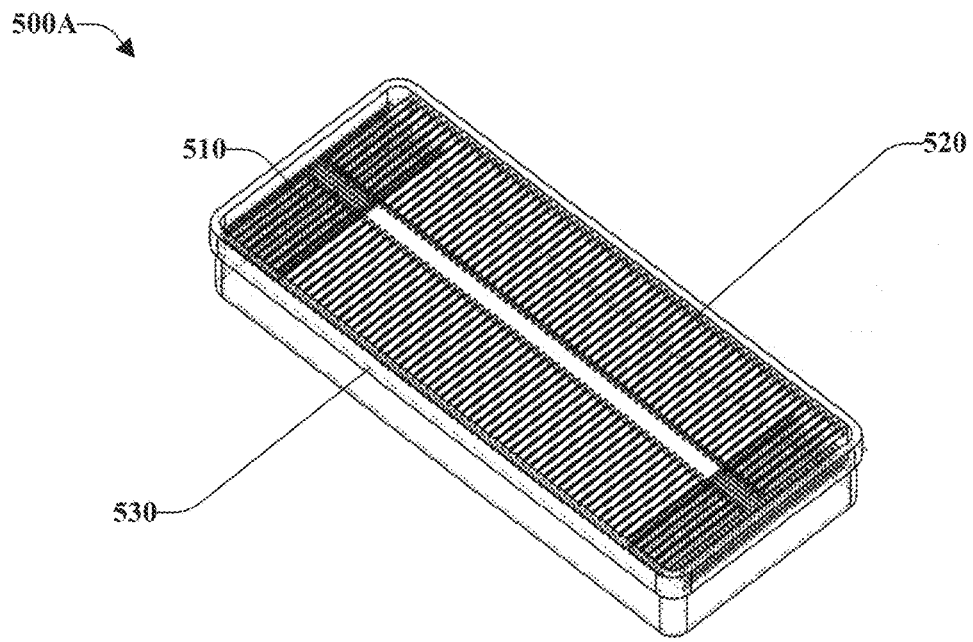
FIG. 5A illustrates an example non-limiting shroud element of a cleaning and disinfecting device.
Figure 5B:
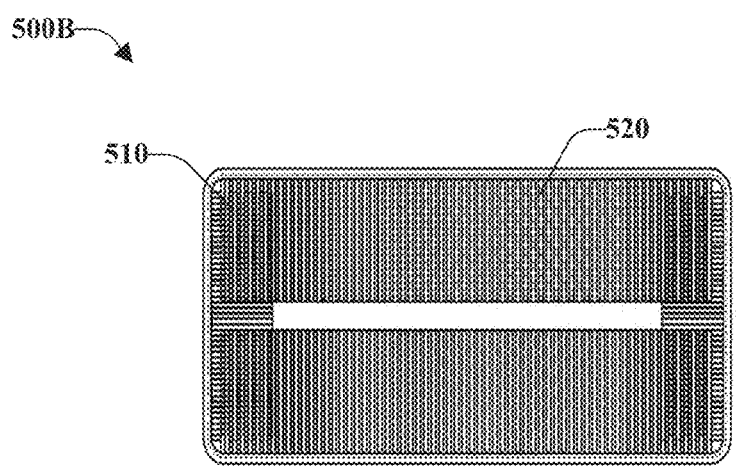
FIG. 5B illustrates an example non-limiting shroud element of a cleaning and disinfecting device from a top view.

Turning now to FIGS. 5A and 5B, illustrated are isolated depictions of containment element 134. In an aspect, FIG. 5A illustrates shroud 530 which can be a removable element. In an aspect, a user can dispose or reuse various shrouds 530 for insertion into containment element 134. In an aspect, by removing and inserting the shroud 530, a user can clean the one or more bristle or dispose of the entire shroud 530 component depending on the level of dirt, unsanitary material, and debris collected by the one or more bristles. In an aspect, the interchangeable shroud 530 can comprise horizontal bristles 520 protruding from the long walls of shroud 530 or overlapping bristles 510 protruding from the shorter walls. The overlapping bristles 510 overlay with the horizontal bristles 520 to create a denser packing of bristles. In an aspect, overlapping bristle 510 and horizontal bristle 520 can vary in length, material composition, size, thickness, density of packing, and other such features. Thus the shrouds depicted at shroud 500A and shroud 500B can be embodied in several manners which are not limited to FIG. 5A and FIG. 5B. In an aspect, FIG. 5B illustrates a nonlimiting embodiment of a downward view of shroud 500B.

Figure 5C:
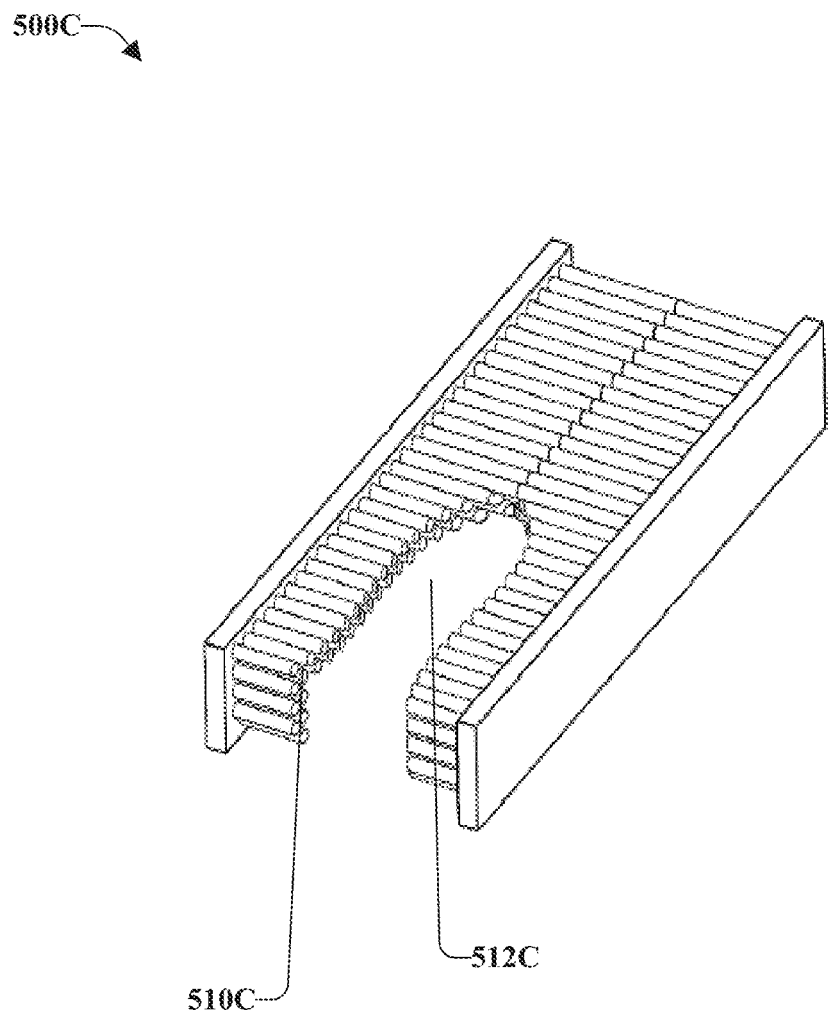
FIG. 5C illustrates an example non-limiting shroud element of a cleaning and disinfecting device with three walls and a fourth wall of one or more bristles.

Turning now to FIG. 5C, illustrated is a non-limiting example of a shroud 500C comprised of three walls, wherein two walls comprise one or more bristles 510C protruding from the inside walls. In an aspect, a third wall comprises a row of brushes that come together. Furthermore, in an aspect, a fourth side does not comprise a fully formed wall, but rather a row of bristles with an opening 512C. In an aspect, opening 512C facilitates easy insertion of footwear item 144. By sliding footwear item 144 into opening 512C, the footwear item 144 is surrounded, nestled and covered with rows of bristles which stabilize the footwear item 144 and provides a curtain of coverage to prevent UV light from emitting beyond the one or more bristles 510 covering.

Figure 5D:
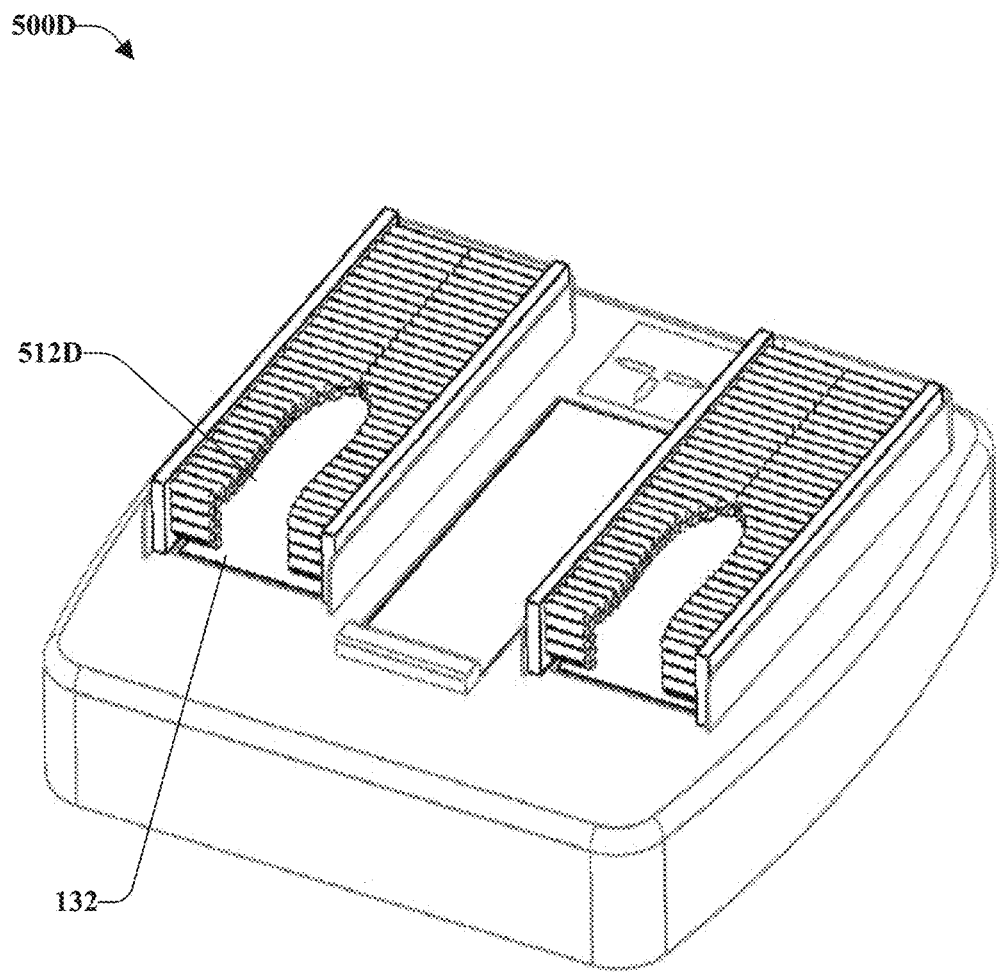
FIG. 5D illustrates an example non-limiting shroud element of a cleaning and disinfecting device with three walls and a wall of one or more bristles, and the incorporation of the shroud element within the cleaning and disinfecting device.

Turning now to FIG. 5D, illustrated is the incorporation of a three-walled shroud within device 500D. In an aspect, the opening 512D sits above the transparent floor layer 132, which in a non-limiting embodiment supports footwear item 144. Thus at device 500D the containment element 134 is absent and the transparent floor layer 132 can sit flush or approximately flush with the casing of device 500D and at the same level as cleaning belt element 120.

Figure 6:
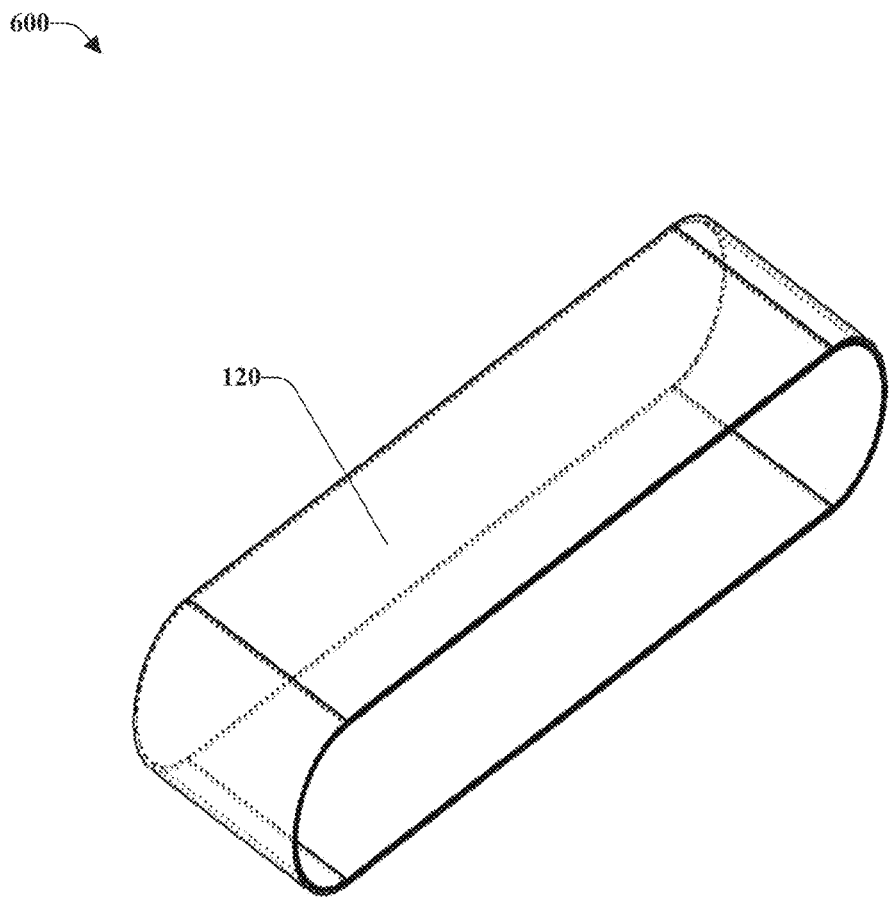
FIG. 6 illustrates an example non-limiting view of a cleaning belt feature of cleaning belt element of a cleaning and disinfecting device.

Turning now to FIG. 6, illustrated is an example of the cleaning belt element 120 of device 600. In an aspect, the cleaning belt element 120 comprises a cleaning belt 120 (illustrated in FIG. 6) wherein the cleaning belt 120 rotates in a continuous loop around a first rotating cylinder 166, which is powered by motor element 156, and a second rotating cylinder 168. In an embodiment, the second rotating cylinder 168 is not powered by a motor element 156. In another embodiment, the second rotating cylinder 168 can be powered by a motor element 156. In an embodiment, a cleaning belt element 120 can employ a wheel and pulley system to rotate the cleaning belt 120 as well.

The aforementioned diagrams have been described with respect to interaction between several components of an automated cleaning and disinfecting device comprised of such elements and components. It should be appreciated that in some suitable alternative aspects of the subject disclosure, such diagrams can include those components and architectures specified therein, some of the specified components/architectures, or additional components/architectures. Sub-components can also be implemented as electrically connected to other sub-components rather than included within parent architecture. Additionally, it is noted that one or more disclosed processes can be combined into a single process providing aggregate functionality.

In view of the exemplary diagrams described supra, a process method that can be implemented in accordance with the disclosed subject matter will be better appreciated with reference to the flow charts of FIGS. 7-10. While for purposes of simplicity of explanation, the methods of FIGS. 7-10 is shown and described as a series of blocks, it is to be understood and appreciated that the claimed subject matter is not limited by the order of the blocks, as some blocks may occur in different orders or concurrently with other blocks from what is depicted and described herein. Moreover, not all illustrated blocks may be required to implement the method described herein. Additionally, it should be further appreciated that the method is capable of being stored on an article of manufacture to facilitate transporting and transferring such method to an electronic device (e.g. electronic cleaning and disinfecting device). The term article of manufacture, as used, is intended to encompass a computer program accessible from any suitable computer-readable device, device in conjunction with a carrier, storage medium, or the like, or a suitable combination thereof.

Figure 7A:
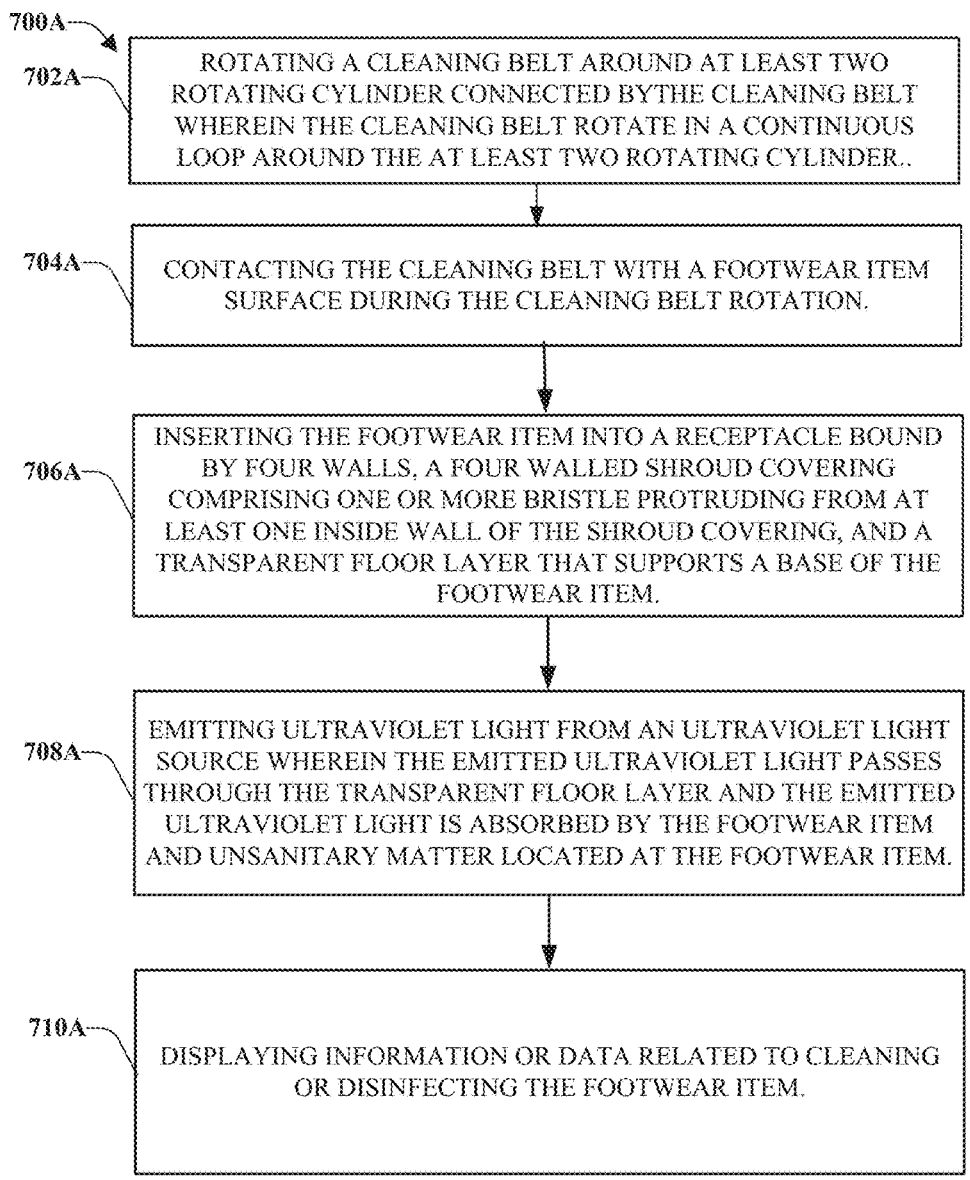
FIG. 7A illustrates an example methodology for rotating a cleaning belt, receiving a footwear item, illuminating the footwear item, and displaying information in accordance with one or more implementations.

Turning now to FIG. 7A, illustrated is a non-limiting flowchart of a sample method 700A for cleaning and disinfecting one or more footwear item. At 702A, a cleaning belt is rotated (e.g. using cleaning belt element 120) around at least two rotating cylinder connected by the cleaning belt wherein the cleaning belt rotate in a continuous loop around the at least two rotating cylinder. At 704A, the cleaning belt contacts a footwear item 144 during the cleaning belt rotation. At 706A, the footwear item 144 is inserted into a receptacle (e.g., containment element 134) bound by four walls, a four walled shroud covering comprising one or more bristle protruding from at least one inside wall of the shroud covering, and a transparent floor layer that supports a base of the footwear item 144. At 708A, ultraviolet light is emitted (e.g. using ultraviolet light element 122) from an ultraviolet light source (e.g. ultra violet light source 126) wherein the emitted ultraviolet light passes through the transparent floor layer and the emitted ultraviolet light is absorbed by the footwear item 144 and unsanitary matter located at the footwear item 144. At 710A, information or data related to cleaning or disinfecting the footwear item can be displayed (e.g. using display element 140).

Figure 7B:
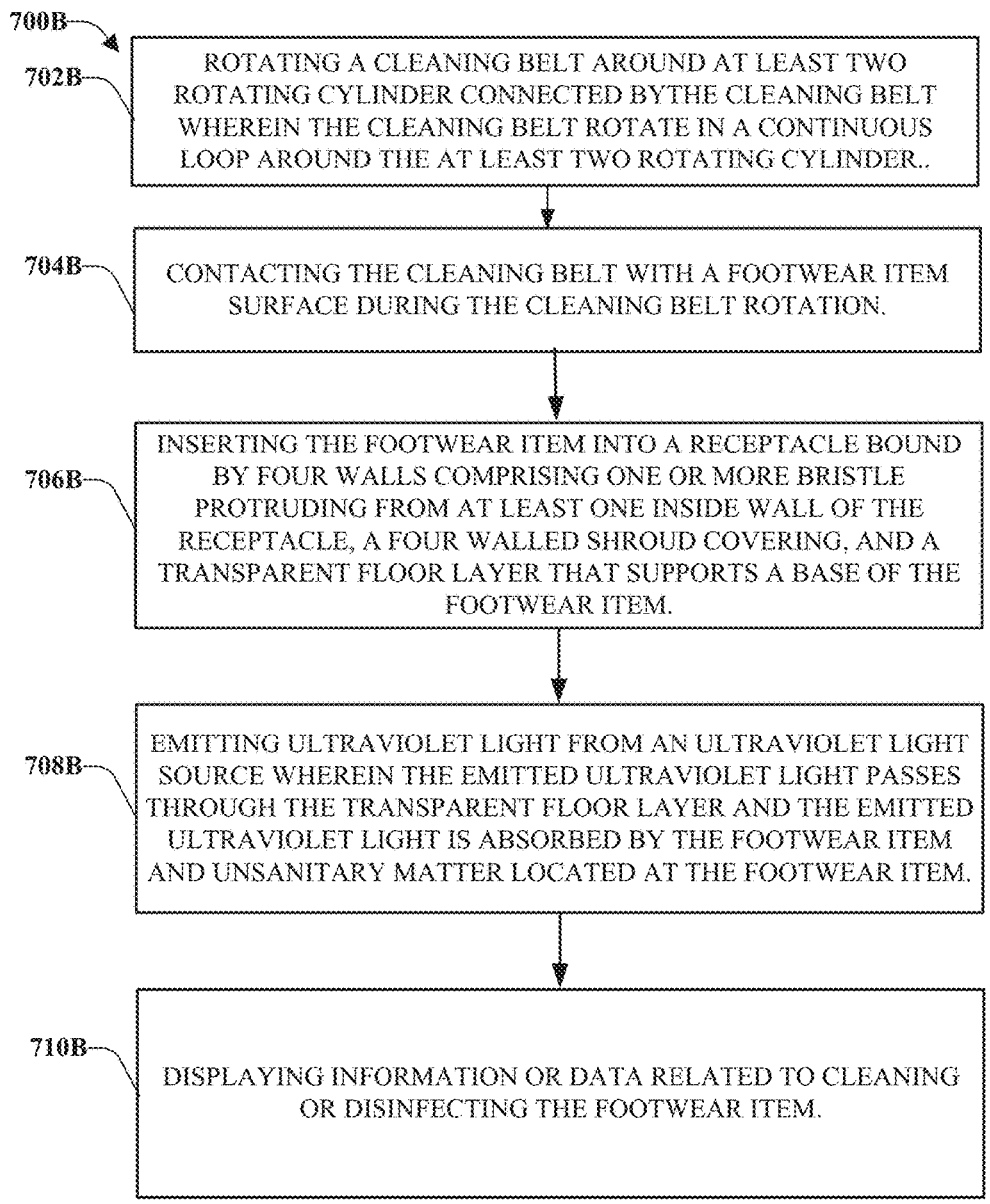
FIG. 7B illustrates an example methodology for rotating a cleaning belt, receiving a footwear item, illuminating the footwear item, and displaying information in accordance with one or more implementations.
Figure 8:
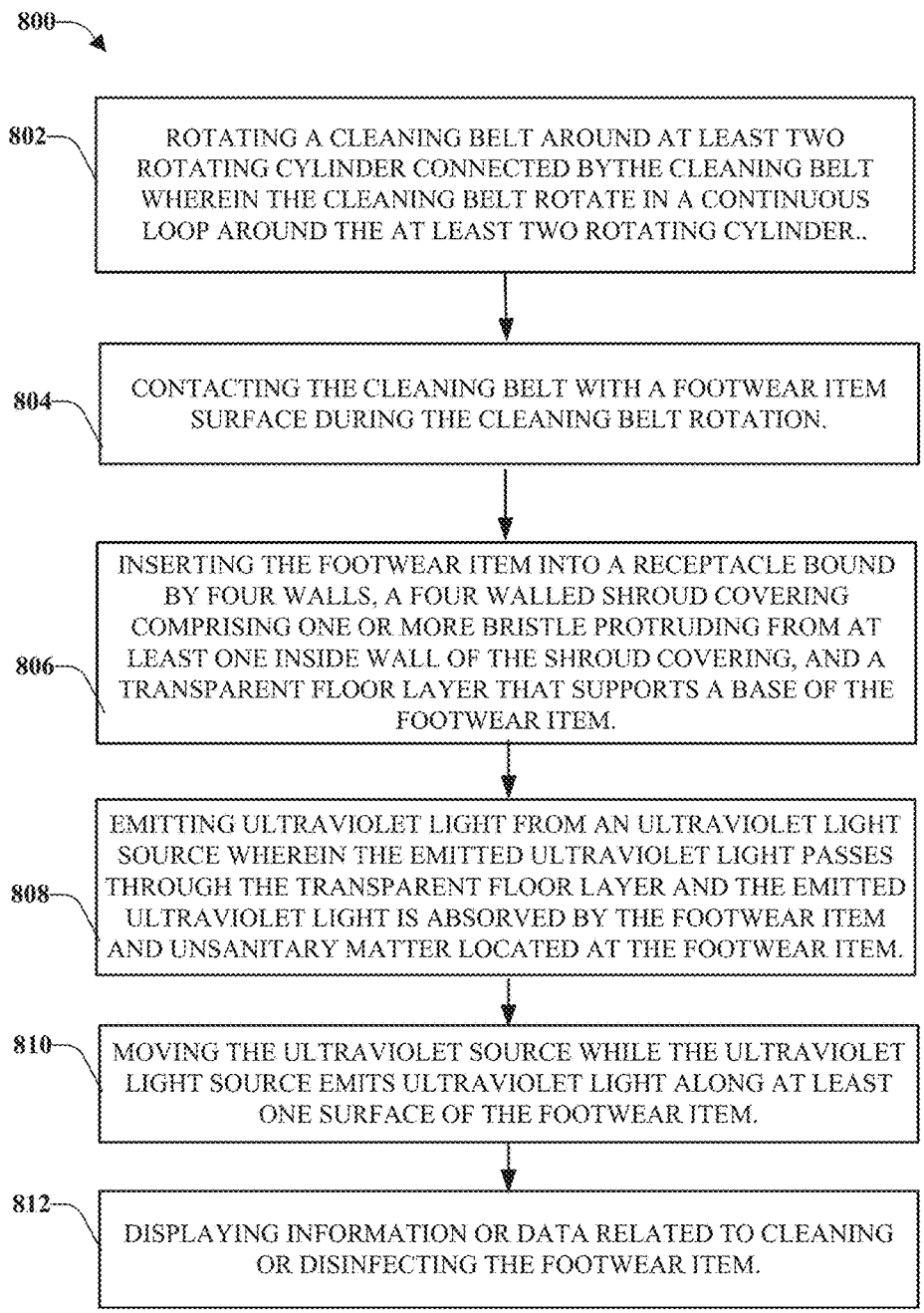
FIG. 8 illustrates an example methodology for rotating a cleaning belt, receiving a footwear item, illuminating the footwear item, moving an illuminated UV light, and displaying information in accordance with one or more implementations of cleaning and disinfecting a footwear item.

Turning now to FIG. 7B, illustrated is a non-limiting flowchart of a sample method 700B for cleaning and disinfecting one or more footwear item. At 702B, a cleaning belt is rotated (e.g. using cleaning belt element 120) around at least two rotating cylinder connected by the cleaning belt wherein the cleaning belt rotate in a continuous loop around the at least two rotating cylinder. At 704B, the cleaning belt contacts a footwear item 144 during the cleaning belt rotation. At 706B, the footwear item 144 is inserted into a receptacle (e.g., containment element 134) bound by four walls, a four walled shroud covering comprising one or more bristle protruding from at least one inside wall of the shroud covering, and a transparent floor layer 132 that supports a base of the footwear item 144. At 708B, ultraviolet light is emitted (e.g. using ultraviolet light Turning now to FIG. 8, illustrated is a non-limiting flowchart of a sample method 800 for cleaning and disinfecting one or more footwear item. At 802, a cleaning belt is rotated (e.g. using cleaning belt element 120) around at least two rotating cylinder connected by the cleaning belt wherein the cleaning belt rotate in a continuous loop around the at least two rotating cylinder. At 804, the cleaning belt contacts a footwear item 144 during the cleaning belt rotation. At 806, the footwear item 144 is inserted into a receptacle (e.g., containment element 134) bound by four walls, a four walled shroud covering comprising one or more bristle protruding from at least one inside wall of the shroud covering, and a transparent floor layer that supports a base of the footwear item 144. At 808, ultraviolet light is emitted (e.g. using ultraviolet light element 122) from an ultraviolet light source (e.g. ultra violet light source 126) wherein the emitted ultraviolet light passes through the transparent floor layer and the emitted ultraviolet light is absorbed by the footwear item 144 and unsanitary matter located at the footwear item 144. At 810, the ultraviolet light source moves along at least one surface of the footwear item while the ultraviolet light source emits ultraviolet light. At 812, information or data related to cleaning or disinfecting the footwear item can be displayed (e.g. using display element 140).

Figure 9:
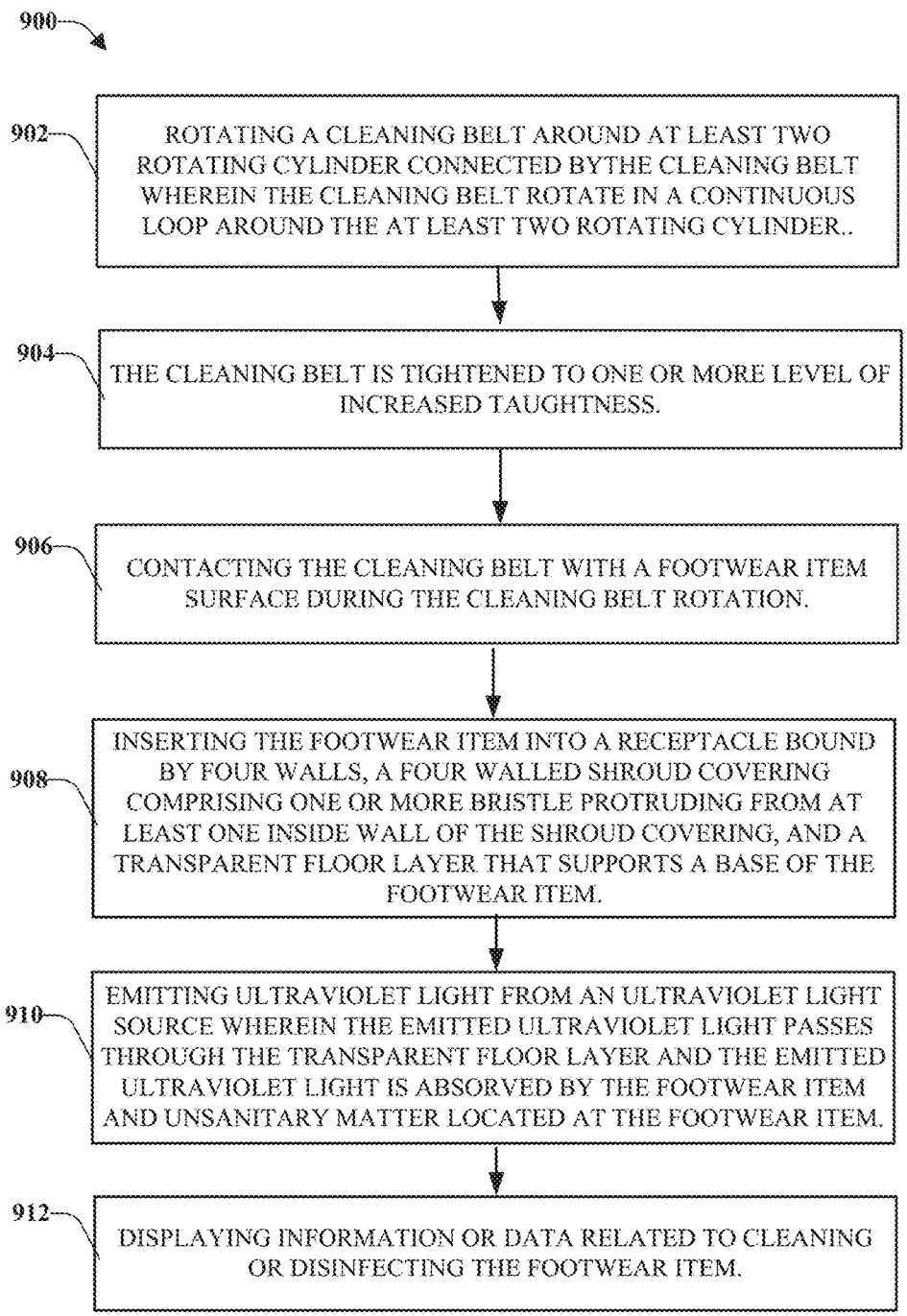
FIG. 9 illustrates an example methodology for rotating a cleaning belt, receiving a footwear item, illuminating the footwear item, moving an illuminated UV light, and displaying information in accordance with one or more implementations.

Turning now to FIG. 9, illustrated is a non-limiting flowchart of a sample method 900 for cleaning and disinfecting one or more footwear item. At 902, a cleaning belt is rotated (e.g. using cleaning belt element 120) around at least two rotating cylinder connected by the cleaning belt wherein the cleaning belt rotate in a continuous loop around the at least two rotating cylinder. At 904, the cleaning belt is tightened (e.g. using tightening arm 220) to one or more level of increased tautness. At 906, the cleaning belt contacts a footwear item 144 during the cleaning belt rotation. At 908, the footwear item 144 is inserted into a receptacle (e.g., containment element 134) bound by four walls, a four walled shroud covering comprising one or more bristle protruding from at least one inside wall of the shroud covering, and a transparent floor layer that supports a base of the footwear item 144. At 910, ultraviolet light is emitted (e.g. using ultraviolet light element 122) from an ultraviolet light source (e.g. ultra violet light source 126) wherein the emitted ultraviolet light passes through the transparent floor layer and the emitted ultraviolet light is absorbed by the footwear item 144 and unsanitary matter located at the footwear item 144. The ultraviolet light source moves along at least one surface of the footwear item while the ultraviolet light source emits ultraviolet light. At 912, information or data related to cleaning or disinfecting the footwear item can be displayed (e.g. using display element 140).

Figure 10:
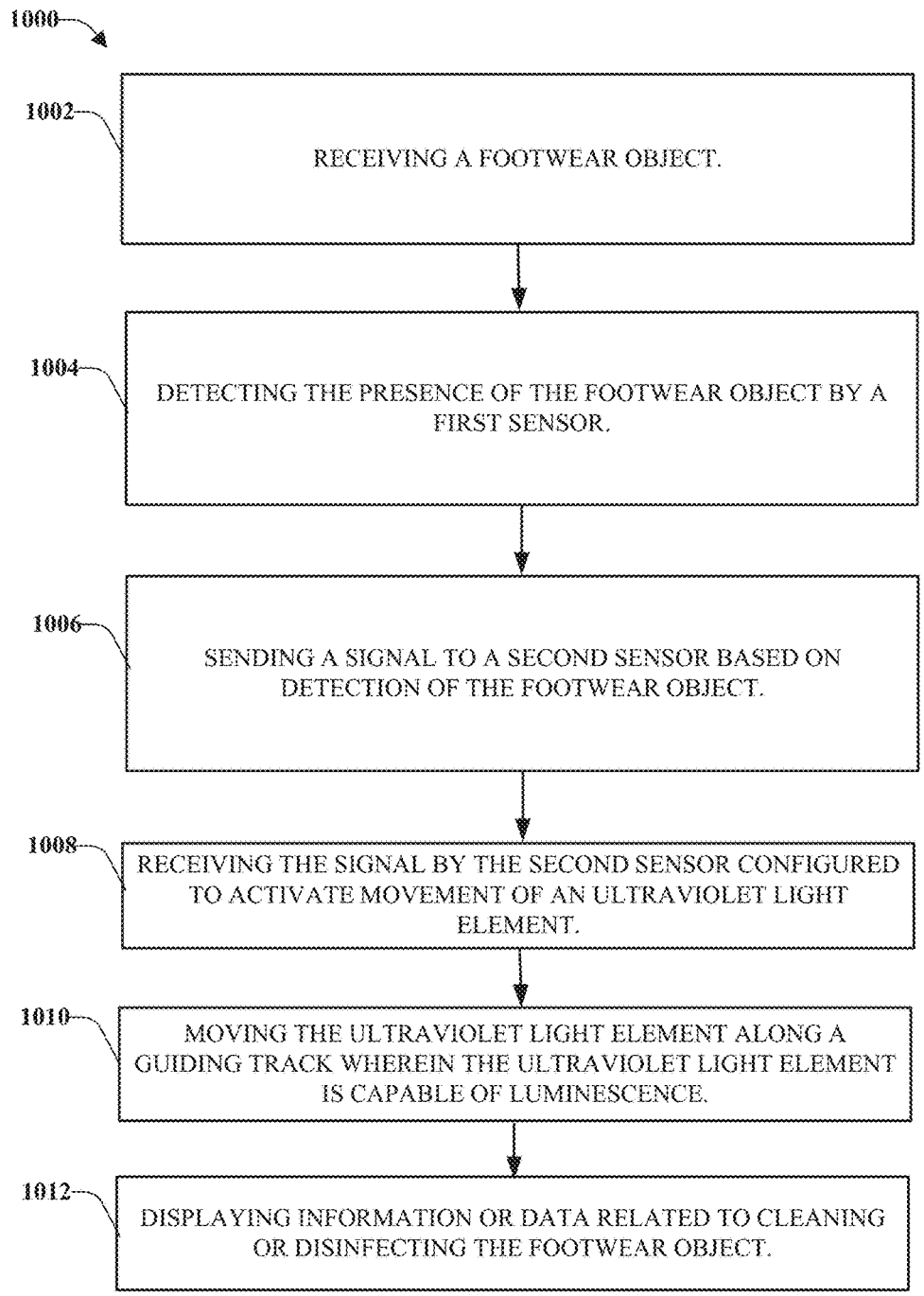
FIG. 10 illustrates an example methodology for receiving a footwear object, detecting the presence of the footwear object, sending a signal to a second sensor, receiving the signal by the second sensor, and moving an ultraviolet light element in accordance with one or more implementations.

Turning now to FIG. 10, illustrated is a non-limiting flowchart of a sample method 1000 for cleaning and disinfecting one or more footwear item. At 1002, a footwear object is received. At 1004, a first sensor detects the presence of the footwear object. At 1006, a signal is sent to a second sensor based on detection of the footwear object. At 1008, the second sensor configured to activate movement of an ultraviolet light element receives the signal. At 1010, the ultraviolet light element is moved along a guiding track wherein the ultraviolet light element is capable of luminescence. At 1012, information or data related to cleaning or disinfecting the footwear object is displayed.

Example Operating Environments

The, systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

Figure 11:
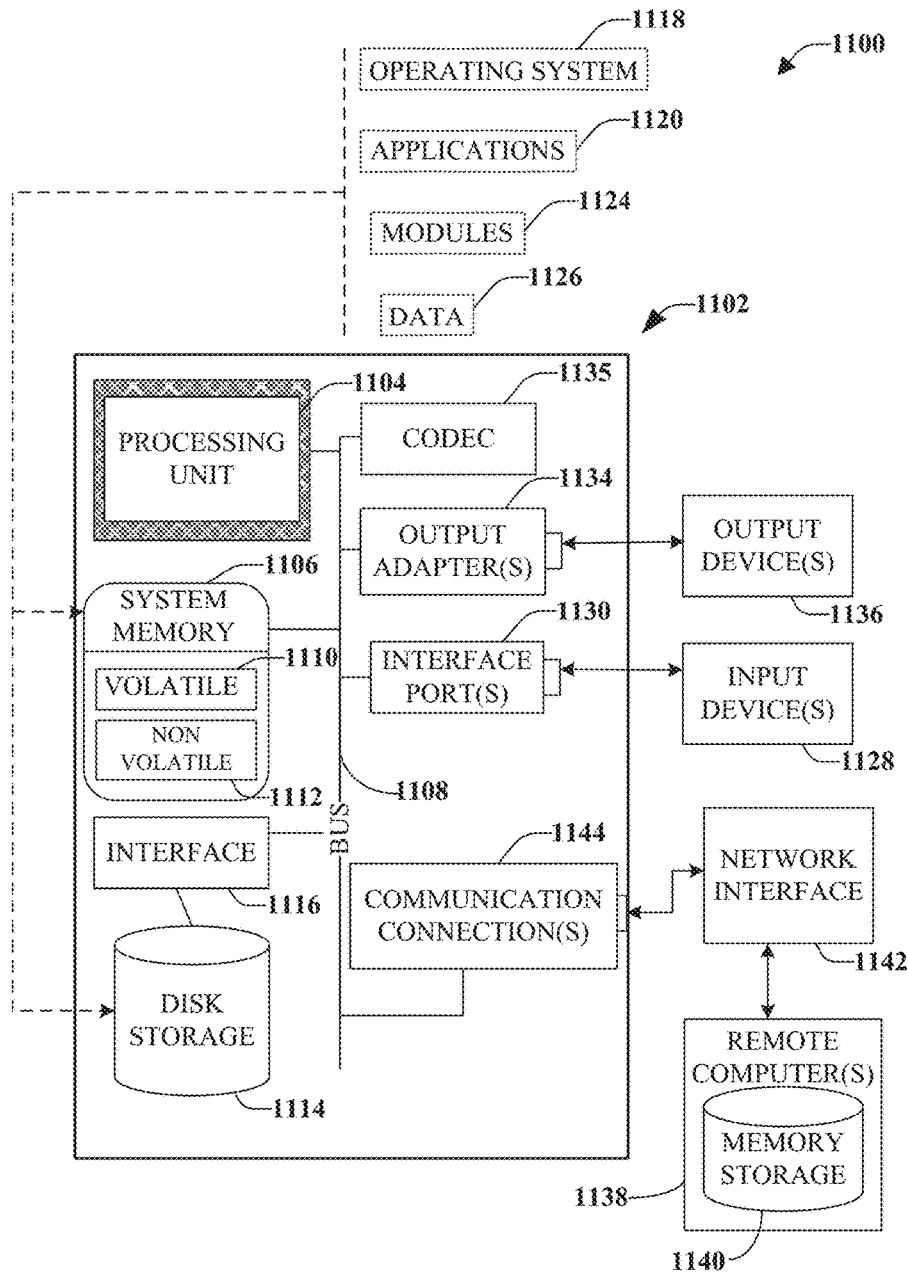
FIG. 11 is a schematic block diagram illustrating a suitable operating environment in accordance with various aspects and embodiments.

With reference to FIG. 11, a suitable environment 1100 for implementing various aspects of the claimed subject matter includes a computer 1102. The computer 1102 includes a processing unit 1104, a system memory 1106, a codec 1105, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1106 includes volatile memory 1110 and non-volatile memory 1112. The basic input/output system (BIOS), containing the basic routines to transfer information between elements within the computer 1102, such as during start-up, is stored in non-volatile memory 1112. In addition, according to present innovations, codec 1105 may include at least one of an encoder or decoder, wherein the at least one of an encoder or decoder may consist of hardware, a combination of hardware and software, or software. Although, codec 1105 is depicted as a separate component, codec 1105 may be contained within non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), or flash memory. Volatile memory 1110 includes random access memory (RAM), which acts as external cache memory. According to present aspects, the volatile memory may store the write operation retry logic (not shown in FIG. 11) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM.

Computer 1102 may also include removable/non-removable, volatile/non-volatile computer storage medium. FIG. 11 illustrates, for example, disk storage 1114. Disk storage 1114 includes, but is not limited to, devices like a magnetic disk drive, solid state disk (SSD) floppy disk drive, tape drive, Jaz drive, Zip drive, LS-70 drive, flash memory card, or memory stick. In addition, disk storage 1114 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1114 to the system bus 1108, a removable or non-removable interface is typically used, such as interface 1116.

It is to be appreciated that FIG. 11 describes software that acts as an intermediary between users and the basic computer resources described in the suitable operating environment 1100. Such software includes an operating system 1118. Operating system 1118, which can be stored on disk storage 1114, acts to control and allocate resources of the computer system 1102. Applications 1120 take advantage of the management of resources by operating system 1118 through program modules 1124, and program data 1126, such as the boot/shutdown transaction table and the like, stored either in system memory 1106 or on disk storage 1114. It is to be appreciated that the claimed subject matter can be implemented with various operating systems or combinations of operating systems.

A user enters commands or information into the computer 1102 through input device(s) 1128. Input devices 1128 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1136 use some of the same type of ports as input device(s). Thus, for example, a USB port may be used to provide input to computer 1102, and to output information from computer 1102 to an output device 1136. Output adapter 1134 is provided to illustrate that there are some output devices 1136 like monitors, speakers, and printers, among other output devices 1136, which require special adapters. The output adapters 1134 include, by way of illustration and not limitation, video and sound cards that provide a means of connection between the output device 1136 and the system bus 1108. It should be noted that other devices and/or systems of devices provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 is logically connected to computer 1102 through a network interface 1142 and then connected via communication connection(s) 1144. Network interface 1142 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the bus 1108. While communication connection 1144 is shown for illustrative clarity inside computer 1102, it can also be external to computer 1102. The hardware/software necessary for connection to the network interface 1142 includes, for exemplary purposes only, internal and external technologies such as, modems including regular telephone grade modems, cable modems and DSL modems, ISDN adapters, and wired and wireless Ethernet cards, hubs, and routers.

Figure 12:
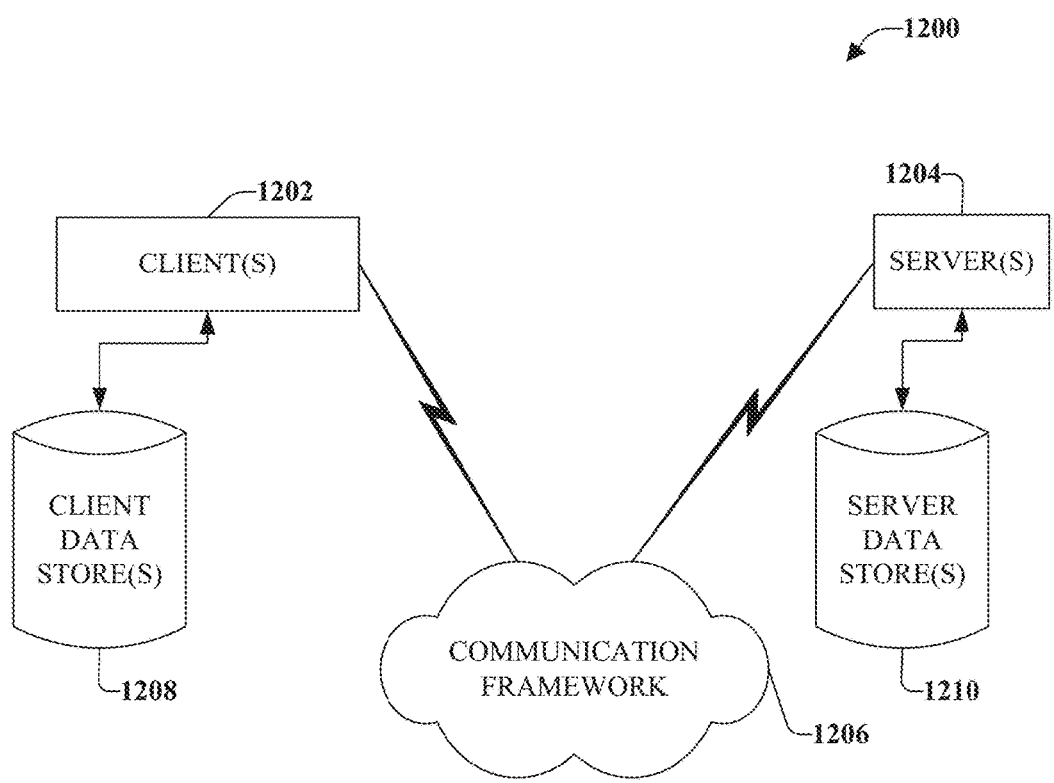
FIG. 12 is a schematic block diagram of a sample-computing environment in accordance with various aspects and embodiments.

Referring now to FIG. 12, there is illustrated a schematic block diagram of a computing environment 1200 in accordance with this disclosure. The system 1200 includes one or more client(s) 1202 (e.g., laptops, smart phones, PDAs, media players, computers, portable electronic devices, tablets, and the like). The client(s) 1202 can be hardware and/or software (e.g., threads, processes, computing devices). The system 1200 also includes one or more server(s) 1204. The server(s) 1204 can also be hardware or hardware in combination with software (e.g., threads, processes, computing devices). The servers 1204 can house threads to perform transformations by employing aspects of this disclosure, for example. One possible communication between a client 1202 and a server 1204 can be in the form of a data packet transmitted between two or more computer processes wherein the data packet may include video data. The data packet can include a metadata, e.g., associated contextual information, for example. The system 1200 includes a communication framework 1206 (e.g., a global communication network such as the Internet, or mobile network(s)) that can be employed to facilitate communications between the client(s) 1202 and the server(s) 1204.

Communications can be facilitated via a wired (including optical fiber) and/or wireless technology. The client(s) 1202 include or are operatively connected to one or more client data store(s) 1208 that can be employed to store information local to the client(s) 1202 (e.g., associated contextual information). Similarly, the server(s) 1204 are operatively include or are operatively connected to one or more server data store(s) 1210 that can be employed to store information local to the servers 1204.

In one embodiment, a client 1202 can transfer an encoded file, in accordance with the disclosed subject matter, to server 1204. Server 1204 can store the file, decode the file, or transmit the file to another client 1202. It is to be appreciated, that a client 1202 can also transfer uncompressed file to a server 1204 and server 1204 can compress the file in accordance with the disclosed subject matter.

Likewise, server 1204 can encode video information and transmit the information via communication framework 1206 to one or more clients 1202.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media.

The invention claimed is:

1. A device comprising:
   a cleaning belt element configured to rotate a cleaning belt in a continuous loop around a first rotating cylinder and a second rotating cylinder, wherein the first rotating cylinder and the second rotating cylinder are connected by the cleaning belt;
   a containment element configured to simultaneously receive a first footwear item and a second footwear item, wherein the containment element comprises a first rigid shroud, a second rigid shroud, and a transparent floor layer, wherein the first rigid shroud comprises a first set of stationary bristles protruding from four inside walls of the first rigid shroud, wherein the second rigid shroud comprises a second set of stationary bristles protruding from four inside walls of the second rigid shroud, wherein the transparent floor layer is configured to support the first footwear item and the second footwear item, wherein the first set of stationary bristles and the second set of stationary bristles configured to circumscribe each of the first footwear item and the second footwear item, wherein a portion of the first set of stationary bristles and the second set of stationary bristles configured to rest above the first footwear item and the second footwear item, and wherein the rigid shroud is raised above the transparent floor layer;
   an ultraviolet light element configured to emit ultraviolet light from an ultraviolet light source, wherein the ultraviolet light source is located below the transparent floor layer, and wherein the emitted ultraviolet light passes through the transparent floor layer, wherein the emitted ultraviolet light is configured to be absorbed by one or more surfaces of the first footwear item and the second footwear item exposed to the emitted ultraviolet light, and wherein the one or more stationary bristle inhibits the emitted ultraviolet light from illuminating an item beyond the one or more stationary bristle and is configured to remove debris from the first footwear item and the second footwear item;
   a display element configured to present information or data in connection with cleaning or disinfecting the first footwear item and the second footwear item; and
   an infrared signal receiver component configured to receive an infrared signal representing instructions transmitted by an application executing on a mobile device, wherein the infrared signal facilitates a set of operational functions corresponding to the cleaning belt element and the ultraviolet light element.

2. The device of claim 1, wherein the first set of stationary bristles and the second set of stationary bristles completely nestle around the first footwear item and the second footwear item, and wherein a portion of the emitted ultraviolet light deflects off of the first set of stationary bristles and the second set of stationary bristles.

3. The device of claim 1, wherein the cleaning belt element employs a material layer attached to one or more surface of the cleaning belt surface.

4. The device of claim 3, wherein the material layer is a hook-and-loop fastener.

5. The device of claim 1, wherein the first set of stationary bristles and the second set of stationary bristles deflect toward the transparent floor layer upon receipt of the first footwear item and the second footwear item by the containment element.

6. The device of claim 1, wherein the display element comprises one or more indicator light, wherein each light respectively illuminates upon completion of cleaning the first footwear item and the second footwear item by either the cleaning belt element or the UV light element.

7. The device of claim 1, further comprising a vacuum element configured to suction matter removed from the first footwear item and the second footwear item.

8. The device of claim 1, further comprising a collection tray element that stores matter removed from the first footwear item and the second footwear item.

9. The device of claim 1, further comprising a first sensor element configured to detect the presence of the first footwear item and the second footwear item within the containment element.

10. The device of claim 9, wherein the first sensor elements transmit a signal to a second sensor element based on the detecting the presence of the first footwear item and the second footwear item.

11. The device of claim 9, further comprising a second sensor element that receives the signal transmitted by the first sensor element.

12. The device of claim 9, further comprising a remote control application executing on a mobile device, wherein the remote control application is configured to activate the first sensor based on a signal transmitted from the remote control element to the first sensor element.

13. The device of claim 1, further comprising a power element configured to apply supply electricity to the device.

14. The device of claim 13, further comprising a motor element configured to convert the electricity into mechanical motion, wherein the mechanical motion can include at least one of activating a one or more pulley, rotating the first rotating cylinder, or rotating the second rotating cylinder.

15. The device of claim 14, further comprising a connector belt element configured to connect motor element to the first rotating cylinder of the cleaning belt element.

16. The device of claim 14, wherein the one or more pulley connects two or more wheel and axle elements capable of rotating a cleaning belt element.

17. The device of claim 1, further comprising a tension arm element configured to maintain the cleaning belt element tautness.

18. The device of claim 17, wherein the tension arm element applies an opposing force to a bottom surface of the cleaning belt element to maintain tautness of the cleaning belt element.

19. The device of claim 1, wherein the ultraviolet light element emits ultraviolet light based on a receipt of a signal by a second sensor element.

20. The device of claim 1, wherein the first set of stationary bristles overlap within the first rigid shroud and the second set of stationary bristles overlap within the second rigid shroud to form a nestled rows of bristles that facilitates a stabilization of the first footwear item and the second footwear item and removal of debris from the first footwear item and the second footwear item.

* * * * *